US 6,673,070 B2

(12) United States Patent
Edwards et al.

(10) Patent No.: US 6,673,070 B2
(45) Date of Patent: Jan. 6, 2004

(54) SPHINCTER TREATMENT APPARATUS

(75) Inventors: Stuart D Edwards, Portola Valley, CA (US); John W. Gaiser, Mountain View, CA (US); David S. Utley, San Carlos, CA (US); Jay J. Qin, Fremont, CA (US)

(73) Assignee: Curon Medical, Inc., Fremont, CA (US)

( * ) Notice: Subject to any disclaimer, the term of this patent is extended or adjusted under 35 U.S.C. 154(b) by 0 days.

(21) Appl. No.: 09/776,140

(22) Filed: Feb. 2, 2001

(65) Prior Publication Data

US 2001/0034518 A1 Oct. 25, 2001

Related U.S. Application Data

(63) Continuation of application No. 09/235,060, filed on Jan. 20, 1999, now Pat. No. 6,254,598, which is a continuation-in-part of application No. 09/026,316, filed on Feb. 19, 1998, now Pat. No. 6,056,744.

(51) Int. Cl.⁷ .............................................. A61B 18/18
(52) U.S. Cl. .......................... 606/41; 602/101; 602/133
(58) Field of Search ............................. 606/41, 42, 45, 606/46, 48–50; 607/101, 102, 115, 116, 133

(56) References Cited

U.S. PATENT DOCUMENTS

| 1,798,902 A | 3/1931 | Raney |
| 3,517,128 A | 6/1970 | Hines |
| 3,901,241 A | 8/1975 | Allen, Jr. |

(List continued on next page.)

FOREIGN PATENT DOCUMENTS

| DE | 43 03 882 | 2/1995 |
| DE | 38 38 840 | 2/1997 |
| EP | 0 139 607 | 5/1985 |

(List continued on next page.)

OTHER PUBLICATIONS

Castell, D.O. "Gastroesophageal Reflux Disease: Current Strategies for Patient Management". Arch Fam Med. 5(4): 221–7.

Dallemagne, B. et al., "Laparoscopic Nissen Fundoplication: Preliminary". Surgical Laparoscopy & Endoscopy. 1991 1(3): 138–43.

Hinder, R.A. et al., "The Technique of Laparoscopic Nissen Fundoplication". Surgical Laparoscopy & Endoscopy. 1992. 2(3): 265–272.

Karlstrom, L.H. et al. "Ectopic jejunal pacemakers and enterogastric reflux after Roux gastrectomy: Effect of intestinal pacing". Surgery 1989. 106(3): 486–495.

(List continued on next page.)

*Primary Examiner*—Michael Peffley
(74) *Attorney, Agent, or Firm*—Ryan Kromholz & Manion, S.C.

(57) ABSTRACT

A sphincter treatment apparatus includes an elongated member having at least one lumen including an inflation lumen and a basket assembly with first and second arms. The basket assembly is coupled to the elongated member and has deployed and non-deployed configurations. An inflatable member is coupled to the elongated member and positioned in an interior of the basket assembly. The inflatable member has deployed and non-deployed states and is coupled to the inflation lumen. In the deployed state, the inflatable member expands the basket assembly to its deployed configuration. A first energy delivery device is positionable in the first arm and advanceable from the first arm to a selected treatment site. A second energy delivery device is positionable in the second arm and advanceable from the second arm to a selected treatment site.

9 Claims, 22 Drawing Sheets

U.S. PATENT DOCUMENTS

| | | |
|---|---|---|
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,790,310 A * | 12/1988 | Ginsburg et al. ......... 219/121.8 |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,236,413 A | 8/1993 | Feiring |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A * | 9/1994 | Pomeranz et al. .......... 600/374 |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A * | 12/1994 | Edwards et al. .............. 606/32 |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,395,361 A * | 3/1995 | Fox et al. ...................... 606/15 |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Ellman et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,448,990 A | 9/1995 | De Faria-Correa |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A * | 1/1998 | Behl et al. ................... 128/898 |
| 5,732,698 A | 3/1998 | Swanson et al. |
| 5,738,096 A | 4/1998 | Ben-Haim |
| 5,823,197 A | 10/1998 | Edwards |
| 5,830,213 A | 11/1998 | Panescu et al. |
| 5,836,874 A | 11/1998 | Swanson et al. |

| | | | |
|---|---|---|---|
| 5,860,974 A | | 1/1999 | Abele |
| 5,871,483 A | | 2/1999 | Jackson et al. |
| 5,957,920 A | | 9/1999 | Baker |
| 6,006,755 A | * | 12/1999 | Edwards ............... 128/898 |
| 6,009,877 A | * | 1/2000 | Edwards ............... 128/898 |
| 6,014,579 A | * | 1/2000 | Pomeranz et al. ........ 600/374 |
| 6,056,744 A | * | 5/2000 | Edwards ................ 606/41 |
| 6,073,052 A | | 6/2000 | Zelickson et al. |
| 6,197,022 B1 | | 3/2001 | Baker |
| 6,355,031 B1 | * | 3/2002 | Edwards et al. ......... 606/102 |

FOREIGN PATENT DOCUMENTS

| | | |
|---|---|---|
| EP | 0 608 609 | 8/1994 |
| WO | 97/43971 | 11/1971 |
| WO | 91/01773 | 2/1991 |
| WO | 92/10142 | 6/1992 |
| WO | 93/08755 | 5/1993 |
| WO | 94/10925 | 5/1994 |
| WO | 94/21165 | 9/1994 |
| WO | 94/21178 | 9/1994 |
| WO | 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 6/1996 |
| WO | 96/29946 | 10/1996 |
| WO | 97/06857 | 2/1997 |
| WO | 97/32532 | 9/1997 |

OTHER PUBLICATIONS

Kelly, KA. et al., "Doudenal–gastric reflux and slowed gastric emptying by electrical pacing of the canine duodenal pacesetter potential". Gastroenterology. 1977. 72(3): 429–33.

Reynolds, J.C. "Influence of pathophysiology, severity, and cost on the medical management of gastroesophageal reflux disease". Am J Health–Syst Pharm. 53 (22 Suppl 3): S5–12.

Urschel, J.D. "Complications of Antireflux Surgery". Am J Surg. 1993. 166(1): 68–70.

Kaneko, et al., Physiological Laryngeal Pacemaker, May 1985, Trans Am Soc. Artif. Intern Organs, vol. XXXI, pp. 293–296.

Mugica et al. Direct Diaphragm Stimulation, Jan. 1987 PACE, vol. 10, pp. 252–256.

Mugica et al., Neurostimulation: An Overview, Chapter 21, Preliminary Test of a Muscular Diaphragm pacing System on Human Patients. 1985. pp. 3. 263–279.

Rice et al., Endoscopic Paranasal Sinus Surgery, Chapter 5, Functional Endoscopic Paranasal Sinus Surgery, The Technique of Messerklinger, Raven Press, 1988, pp. 75–104.

Rice et al., Endoscopic Paranasal Sinus Surgery, Chapter 6, Total Endoscopic Sphenoethmoidectomy, The Technique of Wigand, Raven Press, 1988, pp. 105–125.

* cited by examiner

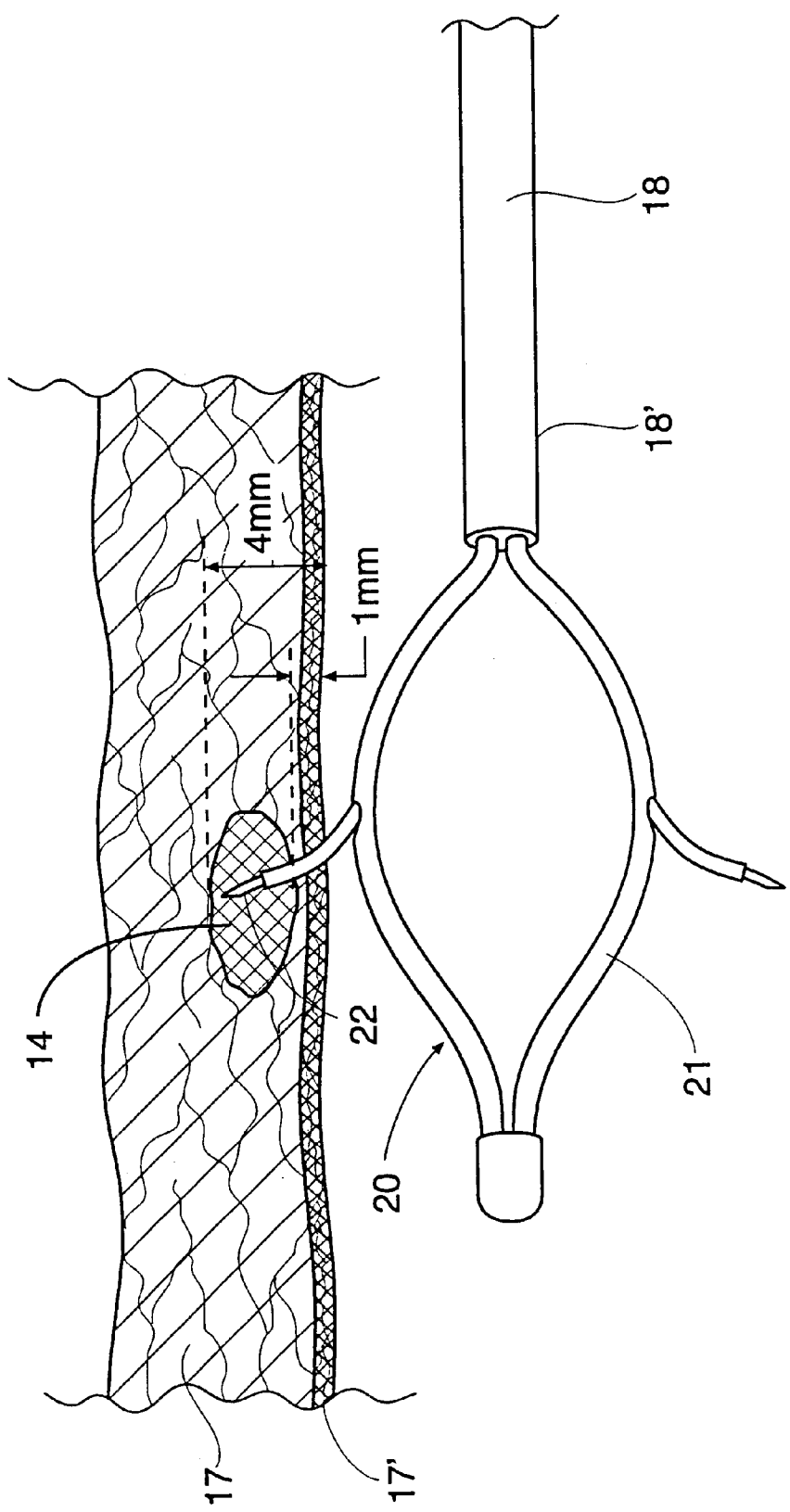

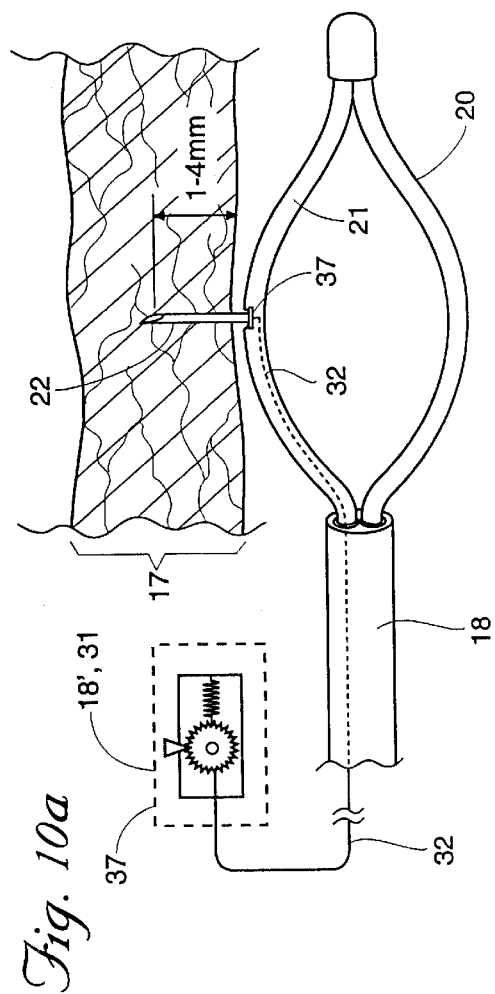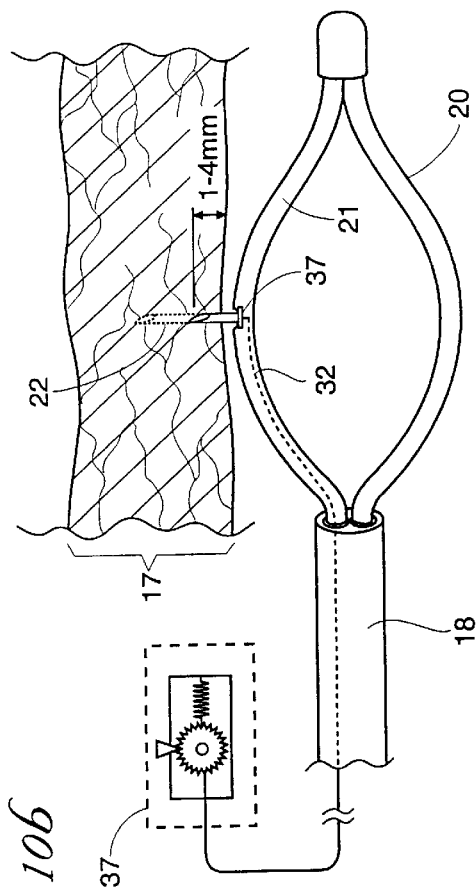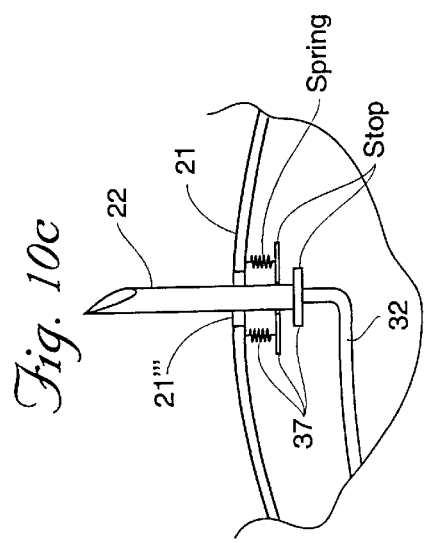

SPHINCTER TREATMENT APPARATUS

CROSS-RELATED APPLICATIONS

This application is a continuation of co-pending U.S. application Ser. No. 09/235,060, filed Jan. 20, 1999, now U.S. Pat. No. 6,254,598, which is a continuation-in-part of U.S. patent application Ser. No. 09/026,316 filed Feb. 19, 1998, now U.S. Pat. No. 6,056,744.

BACKGROUND OF THE INVENTION

1. Field of the Invention

This invention relates generally to an apparatus for the treatment of sphincters, and more specifically to an apparatus that treats esophageal sphincters.

2. Description of Related Art

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: *Gastroesophageal Reflux Disease: Current Strategies For Patient Management*. Arch Fam Med, 5(4):221–7; (April 1996)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20–30% of patients over age 65. Moreover, GERD causes adenocarcinoma, or cancer of the esophagus, which is increasing in incidence faster than any other cancer (Reynolds J C: *Influence Of Pathophysiology, Severity, And Cost On The Medical Management Of Gastroesophageal Reflux Disease*. Am J Health Syst Pharm, 53(22 Suppl 3):S5–12 (Nov. 15, 1996)).

One of the possible causes of GERD may be aberrant electrical signals in the LES or cardia of the stomach. Such signals may cause a higher than normal frequency of relaxations of the LES allowing acidic stomach contents to be repeatedly ejected into the esophagus and cause the complications described above. Research has shown that unnatural electrical signals in the stomach and intestine can cause reflux events in those organs (Kelly K A, et al: *Duodenal-gastric Reflux and Slowed Gastric Emptying by Electrical Pacing of the Canine Duodenal Pacesetter Potential*. Gastroenterology. March 1977; 72(3):429–433). In particular, medical research has found that sites of aberrant electrical activity or electrical foci may be responsible for those signals (Karlstrom L H, et al.: *Ectopic Jejunal Pacemakers and Enterogastric Reflux after Roux Gastrectomy: Effect Intestinal Pacing*. Surgery. September 1989; 106(3): 486–495). Similar aberrant electrical sites in the heart which cause contractions of the heart muscle to take on life threatening patterns or dysrhythmias can be identified and treated using mapping and ablation devices as described in U.S. Pat. No. 5,509,419. However, there is no current device or associated medical procedure available for the electrical mapping and treatment of aberrant electrical sites in the LES and stomach as a means for treating GERD.

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, J D: *Complications Of Antireflux Surgery*, Am J Surg 166(1): 68–70; (July 1993)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. *Surgical Laparoscopy and Endoscopy*, Vol. 1, No. 3, (1991), pp. 138–43 and by Hindler et al. *Surgical Laparoscopy and Endoscopy*, Vol. 2, No. 3, (1992), pp. 265–272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction.

Besides the LES, there are other sphincters in the body which if not functionally properly can cause disease states or otherwise adversely affect the lifestyle of the patient. Reduced muscle tone or otherwise aberrant relaxation of sphincters can result in a laxity of tightness disease states including, but not limited to, urinary incontinence.

There is a need to provide an apparatus to treat a sphincter and reduce a frequency of sphincter relaxation. Another need exists for an apparatus to create controlled cell necrosis in a sphincter tissue underlying a sphincter mucosal layer. Yet another need exists for an apparatus to create cell necrosis in a sphincter and minimize injury to a mucosal layer of the sphincter. There is another need for an apparatus to controllably produce lesions in a sphincter without creating a permanent impairment of the sphincter's ability to achieve a physiologically normal state of closure. Still a further need exists for an apparatus to create a tightening of a sphincter without permanently damaging anatomical structures near the sphincter. There is still another need for an apparatus to create cell necrosis in a lower esophageal sphincter to reduce a frequency of reflux of stomach contents into an esophagus.

SUMMARY OF THE INVENTION

Accordingly, an object of the present invention is to provide an apparatus to treat a sphincter and reduce a frequency of sphincter relaxation.

Another object of the invention is to provide an apparatus to create controlled cell necrosis in a sphincter tissue underlying a sphincter mucosal layer.

Yet another object of the invention is to provide an apparatus to create cell necrosis in a sphincter and minimize injury to a mucosal layer of the sphincter.

A further object of the invention is to provide an apparatus to controllably produce a lesion in a sphincter without creating a permanent impairment of the sphincter's ability to achieve a physiologically normal state of closure.

Still another object of the invention is to provide an apparatus to create a tightening of a sphincter without permanently damaging anatomical structures near the sphincter.

Another object of the invention is to provide an apparatus to create cell necrosis in a lower esophageal sphincter to reduce a frequency of reflux of stomach contents into an esophagus.

Yet another object of the invention is to provide an apparatus to reduce the frequency and severity of gastroesophageal reflux events.

These and other objects of the invention are provided in a sphincter treatment apparatus. The apparatus includes an elongated member with lumen and a basket assembly with first and second arms. The basket assembly is coupled to the elongated member and has deployed and non-deployed configurations. An inflatable member is coupled to the elongated member and positioned in an interior of the basket assembly. The inflatable member has deployed and non-deployed states and is coupled to the elongated member lumen. In the deployed state, the inflatable member expands the basket assembly to its deployed configuration. A first energy delivery device is positionable in the first arm and advanceable from the first arm to a selected treatment site. A second energy delivery device is positionable in the second arm and advanceable from the second arm to a selected treatment site.

BRIEF DESCRIPTION OF THE DRAWINGS

FIG. 3 is a cross-sectional view illustrating the creation of lesions in a sphincter using the apparatus of FIG. 2A.

FIGS. 10a and 10b are cross-sectional views illustrating the use of over indexing with an advancement mechanism to reduce the occurrence of tenting during needle insertion into sphincter wall tissue.

FIG. 10c is a cross-sectional view of an embodiment of the advancement mechanism utilizing mechanical stops and springs.

DETAILED DESCRIPTION

Figure 1:
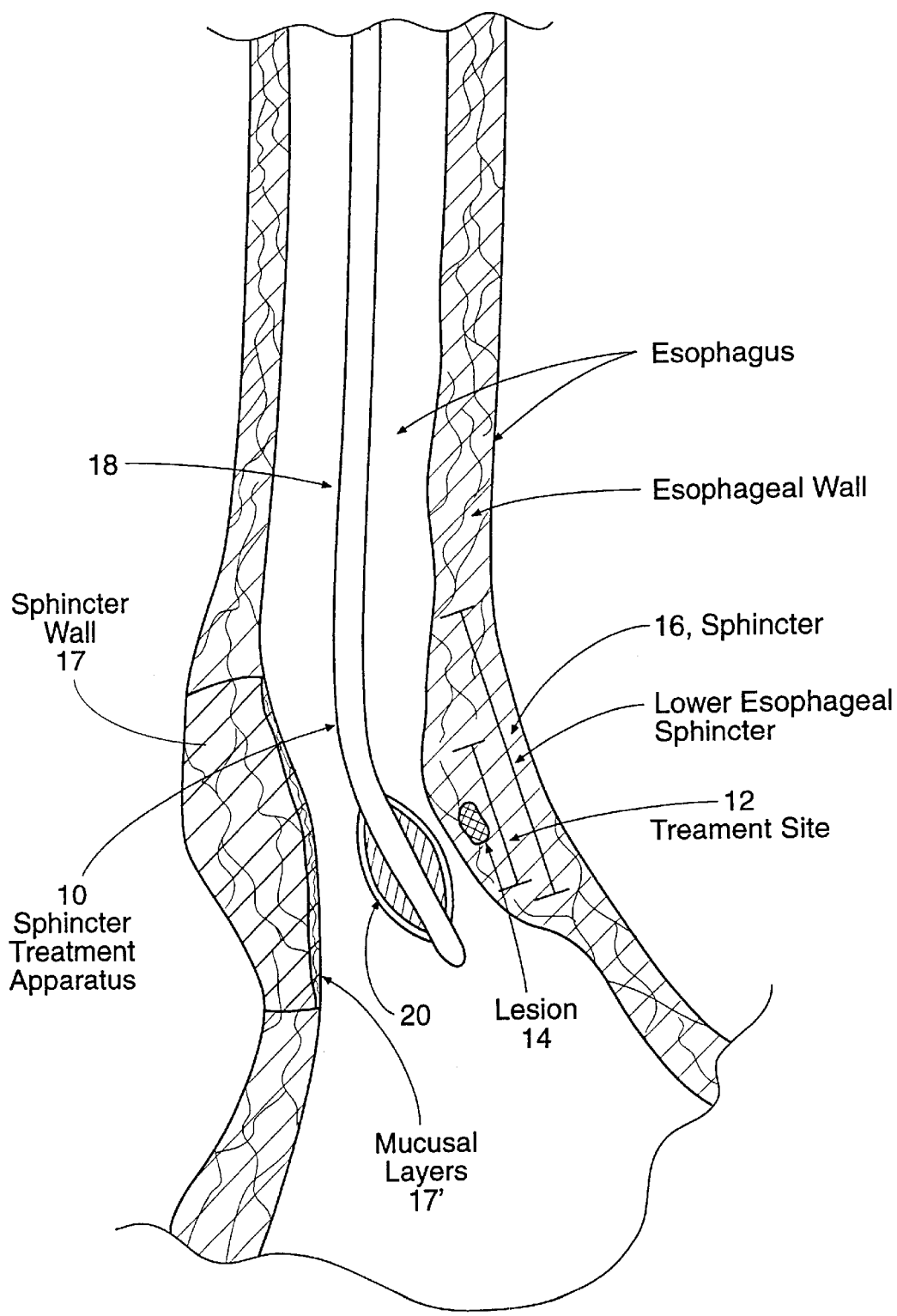
FIG. 1 is an illustrated lateral view of the upper GI tract including the esophagus and lower esophageal sphincter and the positioning of the sphincter treatment apparatus of the present invention in the lower esophageal sphincter.

Referring now to FIG. 1, one embodiment of sphincter treatment apparatus 10 is illustrated. Apparatus 10 delivers energy to a treatment site 12 to produce lesions 14 in a sphincter 16, such as the lower esophageal sphincter (LES) having a wall 17 and mucosal layers 17'. Apparatus 10 includes a flexible elongate shaft 18 which can be an introducer, cannula, catheter and the like.

Figure 2A:
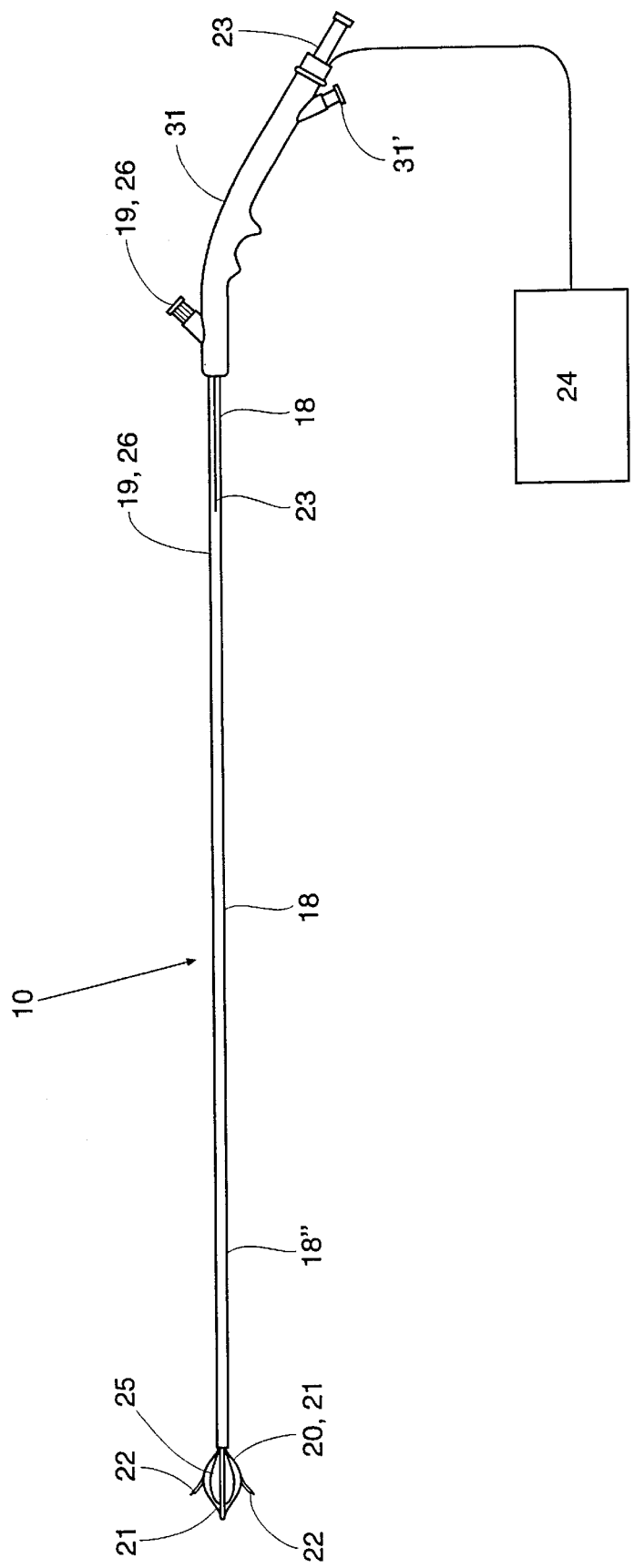
FIG. 2a is a cross-sectional view of one embodiment of the present invention illustrating the inflatable member, the delivery of energy from the basket assembly and advancement of an elongated medical device through a lumen of the elongated member.

As illustrated in FIG. 2a, shaft 18 is coupled to a basket assembly 20. Basket assembly 20 is made of a plurality of arms 21. A plurality of energy delivery devices 22 are positioned and advanced from arms 21 into different circumferential regions of tissue site 12 or other treatment site within the sphincter wall 17 or adjacent anatomical structure. Energy delivery devices 22 are positioned, advanceable and retractable to and from basket assembly 20. Energy delivery devices 22 are positioned a desired depth in a sphincter wall 17 or adjoining anatomical structure. Energy delivery devices 22 are configured to be coupled to an energy source 24. An inflatable or expandable member 25 is also coupled to shaft 18 and is preferably an inflatable balloon well known in the art. Balloon 25 is positioned within the interior of basket assembly 20.

Shaft 18 has a proximal and distal end 18' and 18" and has sufficient length to position expandable basket assembly 20 in the LES and/or stomach including the cardia using a transoral approach. Typical lengths for shaft 18 include, but are not limited to, a range of 40–180 cms. In various embodiments, shaft 18 is flexible, articulated and steerable and can contain fiber optics (including illumination and imaging fibers), fluid and gas paths, and sensor and electronic cabling. In one embodiment, shaft 18 can be a multi-lumen catheter, as is well known to those skilled in the art. Shaft 18 cam also be coupled to a proximal handle 31, which in various embodiments can include handle ports 31' for balloon inflation, and the delivery of cooling and other fluids described herein. Ports 31' can include but are not limited to valves (one-way or two-way), luer fittings and other adaptors and medical fittings known in the art.

Basket assembly 20 is configured to be positionable in a sphincter 16 such as the LES or adjacent anatomical structure, such as the cardia of the stomach. Basket assembly 20 has a central longitudinal axis 20' and is moveable between contracted and expanded positions (also called non-deployed and deployed configurations) substantially there along. In various embodiments, this can be accomplished without a balloon using a pullwire mechanism (not shown) which can include a ratchet mechanism for locking the pull wire in given position. At least portions of apparatus 10 may be sufficiently radiopaque in order to be visible under fluoroscopy and/or sufficiently echogenic to be visible under ultrasonography. Also as will be discussed herein, apparatus 10 can include visualization capability including, but not limited to, a viewing scope, an expanded eyepiece, fiber optics, video imaging and the like. Such viewing means may be delivered through a central lumen 19 within elongated shaft 18 or within or alongside basket assembly 20. In various embodiments, elongated shaft 18 may have multiple lumens 19 which can be configured for the advancement of various elongated medical devices 23 to a treatment site 12 or other area in the body. Elongated medical devices 23 can include guidewires, drug delivery catheters, manometry catheters, pH monitoring catheters, endoscopes, viewing scopes and the like. Lumens 19 can also be configured for the delivery of liquids (including cooling liquids), gases and drugs or medicaments 13 to a treatment site 12 or other area of the body. In one embodiment lumen 19 can be configured as an inflation lumen described herein to inflate inflatable member 25 using a liquid or gaseous inflation media.

Figure 2B:
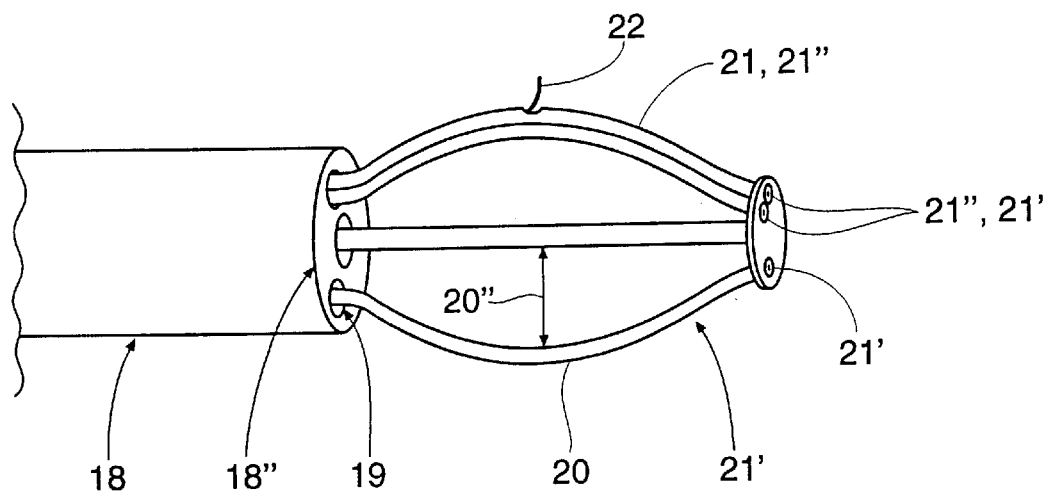
FIG. 2b is a perspective view of an embodiment of the invention illustrating the use of lumens and tubes in the basket arms.

Referring now to FIG. 2b, arms 21 can have one or more channels or lumens 21' or may comprise multiple tubes 21" to allow multiple functions to be performed at each arm such as needle deployment and the delivery of cooling or electrolytic fluids. Also, arms 21 may form a variety of geometric shapes including, but not limited to, curved, rectangular, trapezoidal and triangular. Arms 21 can also have any number of different cross sectional geometries including, but not limited to, circular, rectangular and crescent-shaped. In one embodiment, arms 21 are of a sufficient number, such as two or more, and with adequate spring force (0.01 to 0.5 lbs. force) to collectively exert enough force on the sphincter wall 17 to open and efface the folds of sphincter 16. Arms 21 can be made of a variety of different materials including but not limited to, spring steel, stainless steel, superelastic shape memory metals such as nitinol, un-reinforced plastic tubing, or wire reinforced plastic tubing as is well known to those skilled in the art. Arms 21 can also have an outwardly bowed shaped memory for expanding basket assembly 20 into engagement with the sphincter wall, with the amount of bowing or camber 20" being selectable. Arms 21 may be preshaped at time of manufacture or shaped by the physician.

In another embodiment, arms 21 may have an external layer of the texturized material that has sufficient friction to at least partially immobilize the area of sphincter wall near and around that contacted by an arm 21. Suitable materials for the texturized material include knitted Dacron® and Dacron velour.

Figure 2C:
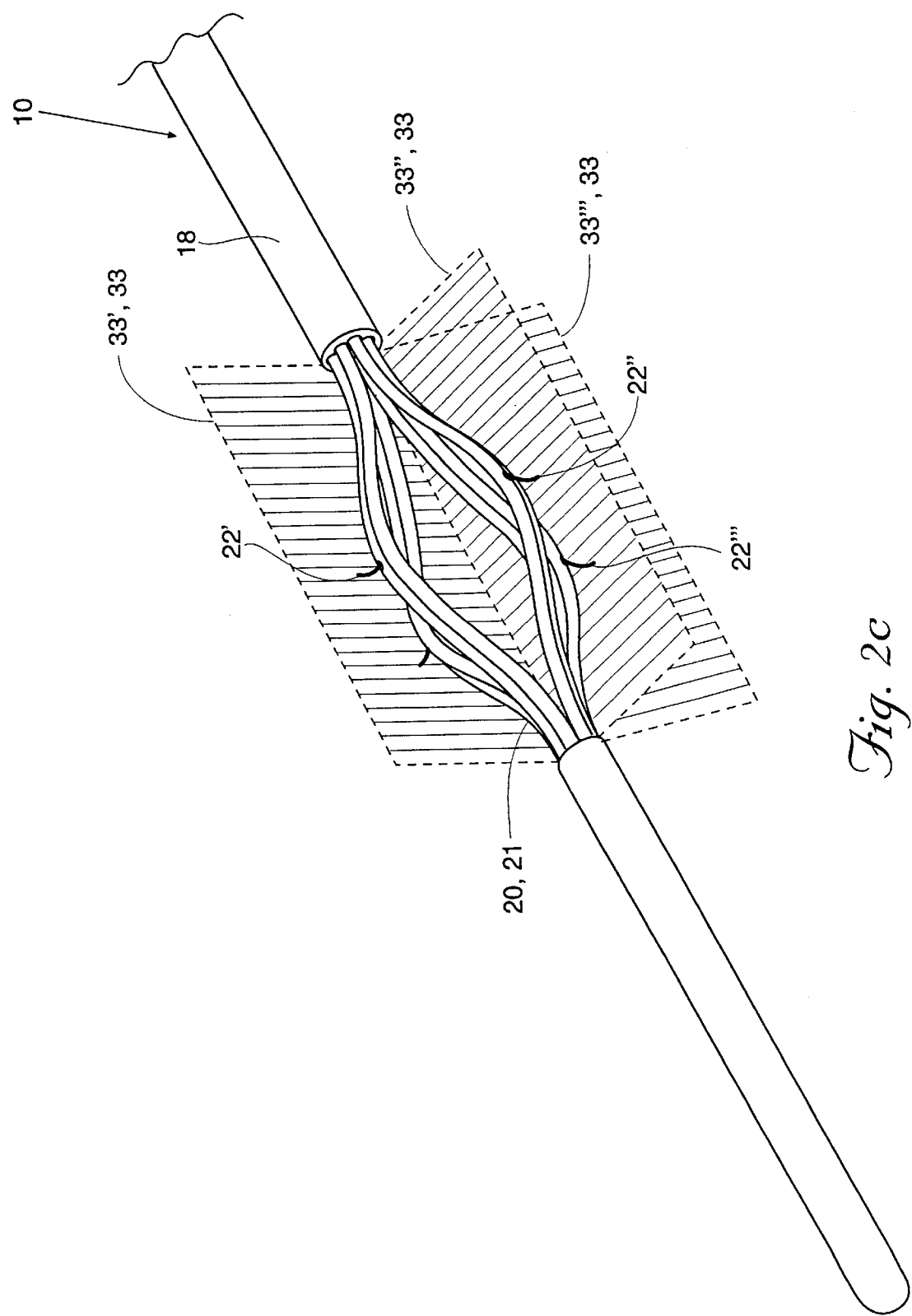
FIG. 2c is a perspective view illustrating an embodiment of the invention where the energy delivery devices are deployed in multi-level geometries.

In one embodiment, illustrated in FIG. 2c, energy delivery devices 22 are deployed in multi-level geometries. As shown, first, second and third levels of energy delivery devices 22', 22" and 22''' are deployed. The energy delivery devices 22 of each level define a plane of deployment 33 which can include first second and third deployment planes 33', 33" and 33'''. Each plane of deployment for the different multi-levels can be parallel. In various embodiments, first, second and third levels of energy delivery devices 22', 22" and 22''' are deployed simultaneously or alternatively sequentially.

Turning now to a discussion of energy delivery, suitable energy sources 24 and energy delivery devices 22 that can be employed in one or more embodiments of the invention include: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source coupled to a heating element positioned either on the arms to heat tissue directly or within the balloon to heat the inflation medium, (x) a microwave source providing energy from 915 MHz to 2.45 GHz and coupled to a microwave antenna, or (xi) an ultrasound power source coupled to an ultrasound emitter, wherein the ultrasound power source produces energy in the range of 300 KHZ to 3 GHz. For ease of discussion for the remainder of this specification, the power source utilized is an RF source and energy delivery device 22 is one or more RF electrodes 22. However, all of the other herein mentioned energy sources and energy delivery devices are equally applicable to sphincter treatment apparatus 10.

For the case of RF energy, RF electrode 22 may be operated in either bipolar or monopolar mode with a ground pad electrode. In a monopolar mode of delivering RF energy, a single electrode 22 is used in combination with an indifferent electrode patch that is applied to the body to form the other electrical contact and complete an electrical circuit. Bipolar operation is possible when two or more electrodes 22 are used. Electrodes 22 can be attached to an electrode delivery member (describe herein) by the use of soldering methods which are well known to those skilled in the art. Suitable solders include Megabond Solder supplied by the Megatrode Corporation (Milwaukee, Wis.). Other joining methods include, but are not limited to, welding and adhesive bonding (including the use of conductive adhesives known in the art). In various embodiments, the electrode to delivery member joint can be conductive (for the case where electrodes 22 are activated simultaneously) or nonconductive (for the case where electrodes 22 are activated individually). In the latter case, electrodes are attached to individual conductors and are electrically isolated from each other (e.g. other electrodes).

Figure 2D:
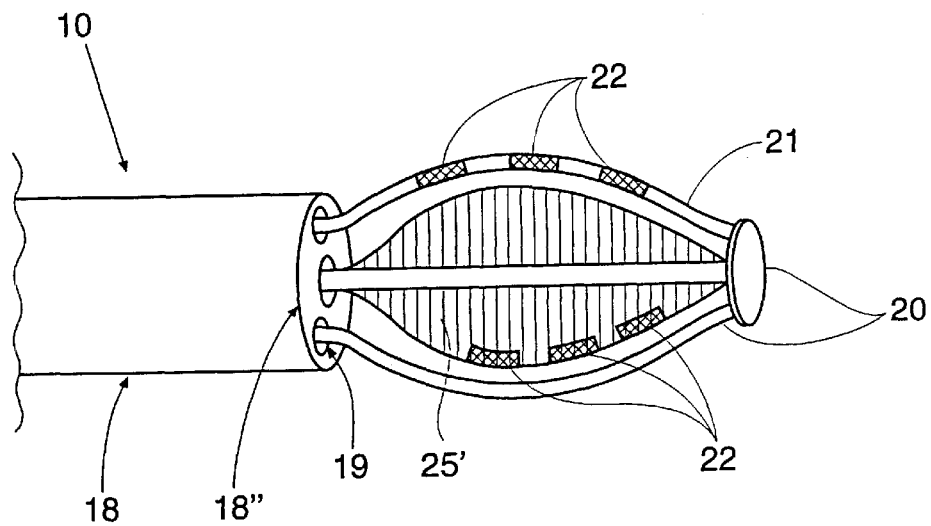
FIG. 2d is a cross-sectional view illustrating the attachment of energy delivery devices to the basket arms and balloon.
Figure 2E:
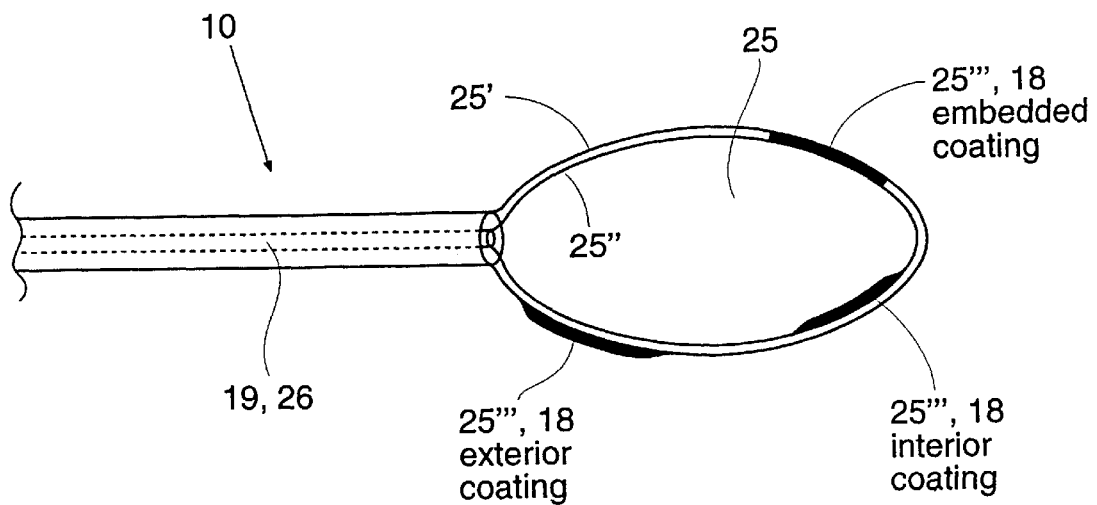
FIG. 2e is a cross-sectional view illustrating an energy delivery device comprising a conductive coating on or in the balloon.

Referring now to FIGS. 2d and 2e, in other embodiments, electrodes 22 can be attached to arms 21, or balloon 25 using adhesive bonding or other joining methods known in the art. In one embodiment all or a portion of electrodes 22 can integral to or otherwise built into arms 21. This can be accomplished using a variety of plastic processing methods known in the art including, the use of heated capture tubes and/or heated collets or notching fixtures. In one embodiment, electrodes 22 can be substantially flush with the surface of arms 21. Electrodes 22 can also be attached to the exterior surface 25' of balloon 25. In one embodiment shown in FIG. 2e, electrode 22 may comprise a conductive coating or layer 25'" that is applied to all or a portion of the or exterior 25' or interior 25" surface of balloon 25 or is otherwise incorporated/embedded into the wall of balloon 25. Coating 25'" may include conductive polymers or metals (e.g. gold, platinum, etc.) and may applied using, sputtering, spraying or electro/chemical deposition techniques known in the art. In one embodiment, conductive coating 25'" can be applied to discrete areas on the exterior surface 25' of balloon 25 using masking and electro/chemical deposition techniques known in the art.

RF electrodes 22 can have a variety of shapes and sizes. Possible shapes include, but are not limited to, circular, rectangular, conical and pyrarnidal. Electrode surfaces can be smooth or textured and concave or convex. The conductive surface area of electrode 22 can range from 0.1 mm$^2$ to 100 cm$^2$. It will be appreciated that other geometries and surface areas may be equally suitable.

Figure 2F:
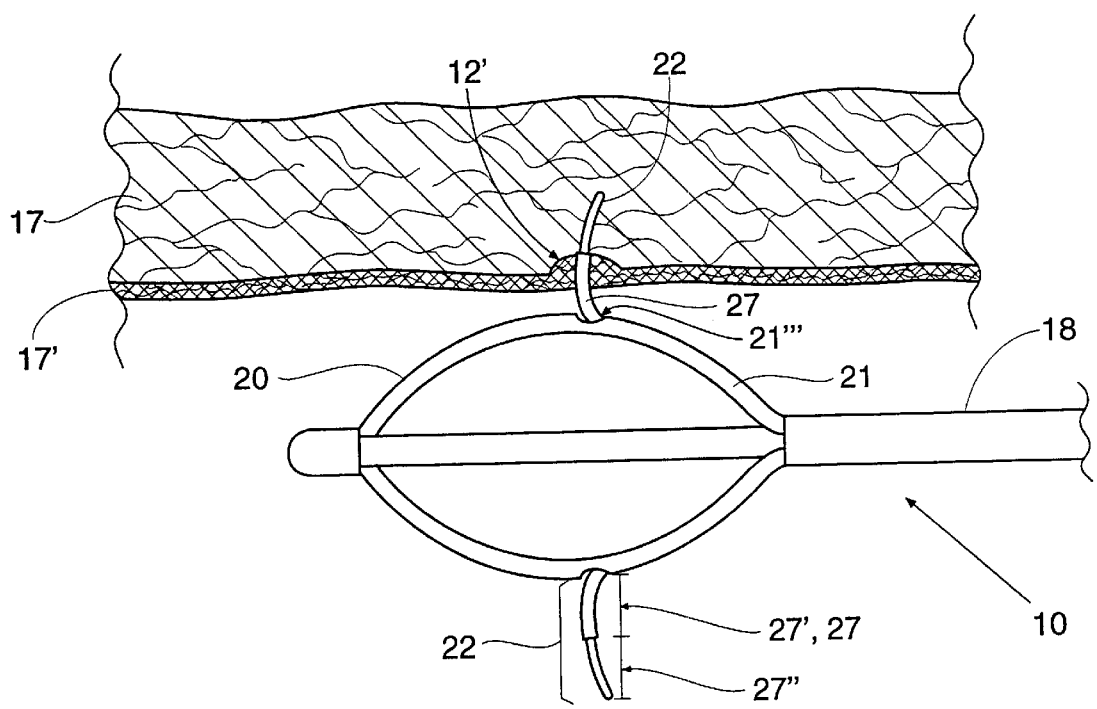
FIG. 2f is a cross-sectional view illustrating the use of needles as RF energy delivery devices, including the use of hollow and insulated needles.

Referring now to FIG. 2f in one embodiment, RF electrodes 22 can be in the shape of needles and of sufficient sharpness and length to penetrate into the smooth muscle of the esophageal wall, sphincter 16 or other anatomical structure. An insulation sleeve 27 can be positioned at an exterior of each RF electrode 22. The use of insulation sleeve 27 creates an insulated segment 27' of RF electrode 22 and provides protection of the mucosal layer 17' of sphincter 16. For purposes of this disclosure, an insulator or insulation layer is a barrier to either thermal, RF or electrical energy flow. The insulated segment of RF electrode 22 is of sufficient length to extend into the sphincter wall 17 and minimize transmission of RF energy to a protected site 12' near or adjacent to insulated segment 27'. Typical lengths for insulated segment 27' include, but are not limited to, 1–8 mms, with preferred embodiments of 2, 5 and 8 mms. Typical lengths for the uninsulated portion or segment 27" of electrode 22 include 2 to 6 mms, with preferred embodiments of 3, 4 and 5 mms.

Suitable materials for RF electrodes 22 include, but are not limited to, 304 stainless steel and other stainless steels known to those skilled in the art. Suitable materials for insulation sleeve 27 include, but are not limited to, polyimides and parylene; and in a preferred embodiment, PET (polyethylene terephthalate).

Referring back to FIG. 2a, balloon 25 can be coupled to and inflated by an inflation lumen 26 (which can also be lumen 19) using gas or liquid as is known in the art. This results in balloon 25 going from an non-deployed to a deployed state. Inflation lumen 26 can be coupled to handle port 31' which can be a one-way valve known in the art. All or a portion of balloon 25 can be made of a non compliant material (as is known in the art) in order to achieve a predictable fixed balloon diameter. In various embodiments, such non compliant materials include PET, irradiated polyethylene, polyurethane and others known in the art. In alternative embodiments, balloon 25 can be configured to have an adjustable diameter by constructing all or a portion of balloon 25 from compliant materials. Such compliant materials include latex, silicone, C-flex and other thermoplastics and elastomers known in the art. All or a portion of balloon 25 may be made of a textured material, or have a texturized layer that when engaged with a sphincter wall 17 provides sufficient friction to at least partially immobilize the surface of the sphincter wall. Suitable materials for the texturized layer include knitted Dacron® and Dacron velour.

Figure 2G:
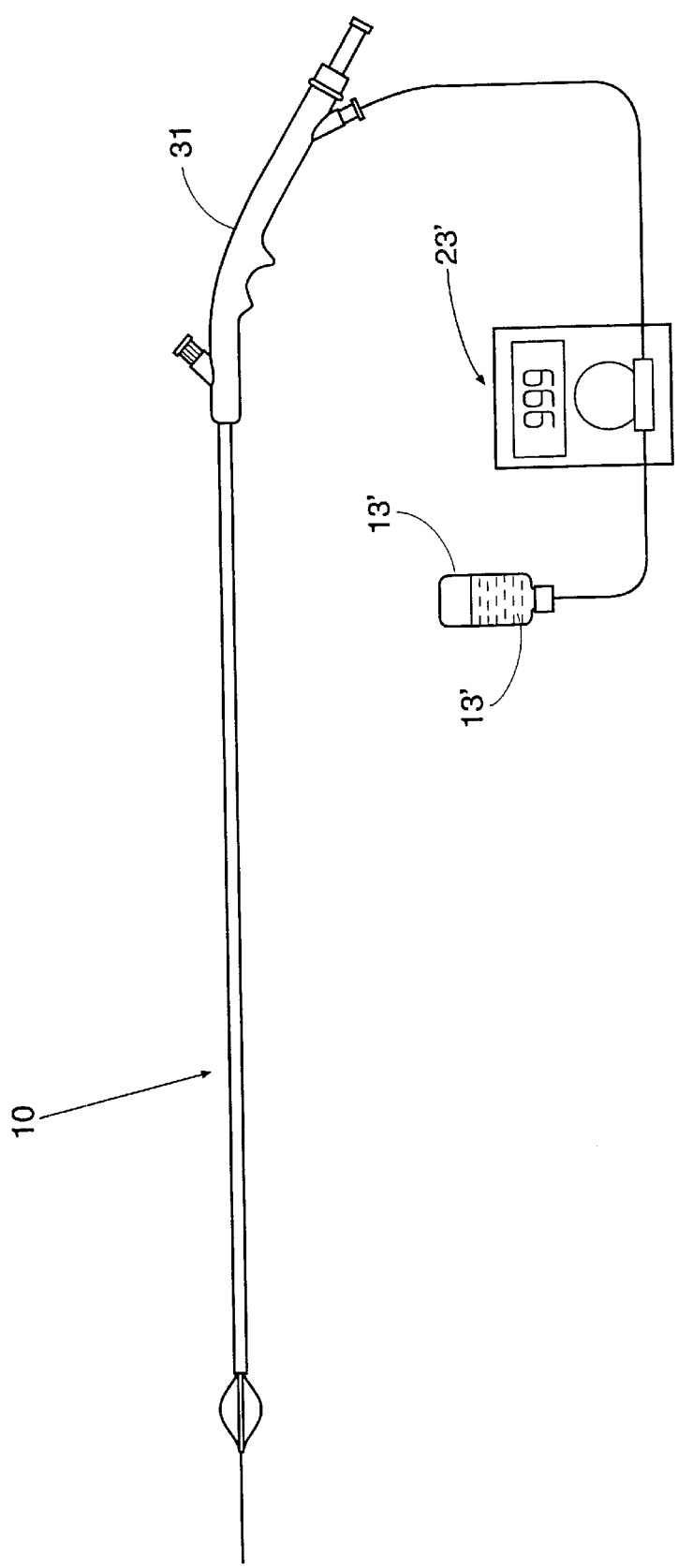
FIG. 2g is a cross-sectional view illustrating the use of a drug delivery device and medicament coupled to the apparatus of FIG. 2A.

Referring now to FIG. 2g, apparatus 10 can also be configured to be coupled to a medical device 23' including a drug delivery device, 23'. In various embodiments, drug delivery device 23' can include an infusion pump, syringe (manual or motorized) IV bag with a pressure clamp or other drug delivery device known in the art. Drug delivery device 23' can also be coupled to medicament 13 and or medicament reservoir 13' containing medicament 13.

Referring now to FIG. 3, energy delivery devices 22 are advanced into sphincter wall 17 a sufficient distance to create lesions 14 while preserving sphincter mucosal layer 17'. In one embodiment, lesions 14 are created circumferentially and equally distanced in order to create an even tightening of sphincter 16. In another embodiment, lesions are created that are about 1 mm below the surface of sphincter wall mucosal layer 17' and extend to a depth of about 4 mm within sphincter wall 17.

Figure 4:
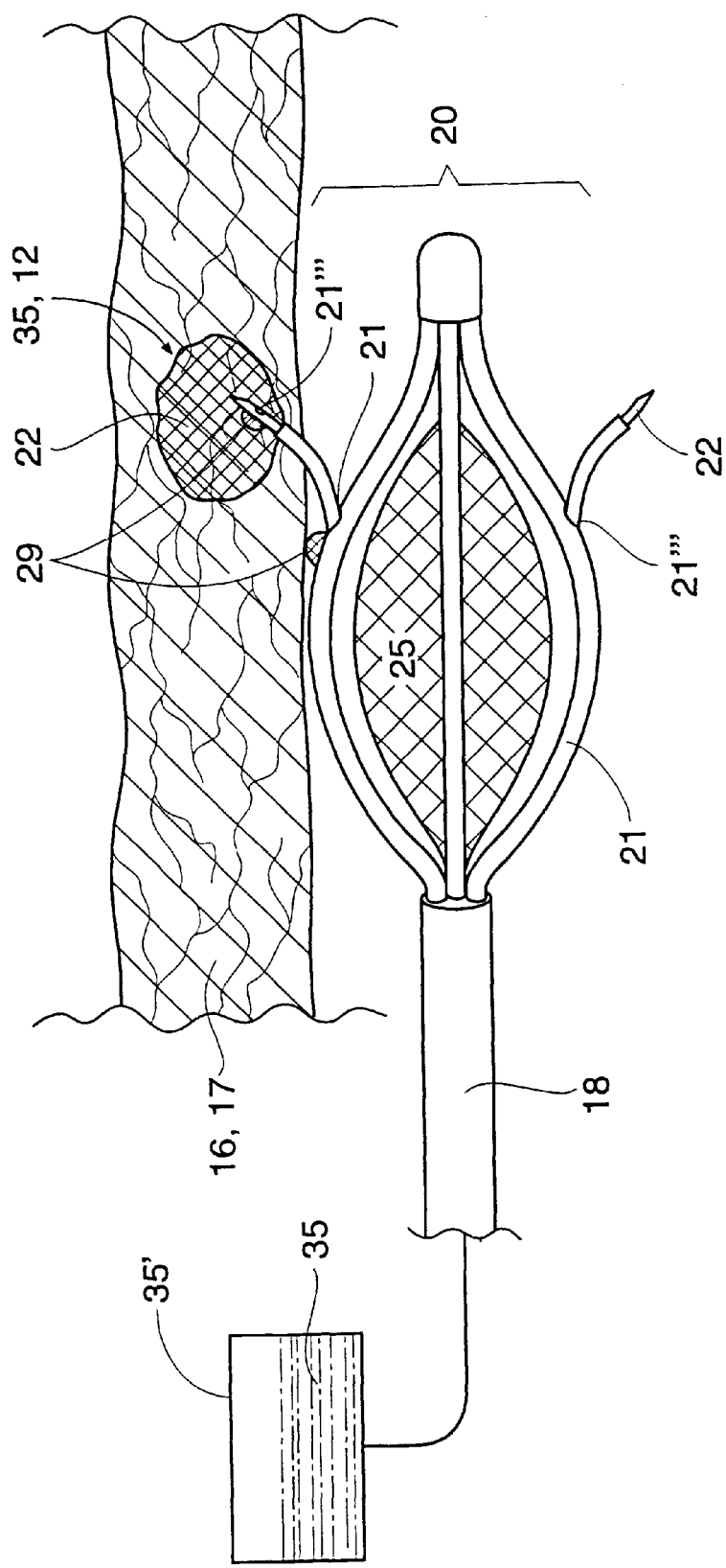
FIG. 4 is a cross-sectional view illustrating the use of a cooling media and its introduction via the basket arms or energy delivery devices.

Referring now FIG. 4, a fluidic media 35, including but not limited to, a cooling media 35, can be introduced through arms 21. Cooling media 35 is introducible through ports 21'" or apertures 21'" from which energy delivery devices 22 are advanced or through distinct and separate apertures 21'". Arms 21 can be fluidically coupled to cooling media 35 and/or a cooling media reservoir 35' via arm lumens 21'. Other suitable fluidic media 35 include, but are not limited to, sterile water, saline, anti-infective agents, echogenic media, steroids, local anesthetics and the like. The use of cooling preserves the mucosal layers 17' of sphincter 16 and protects, or otherwise reduces the degree of cell damage in the vicinity of lesion 14.

Similarly, it may also be desirable to cool all or a portion of RF electrode 22. The rapid delivery of heat through RF electrodes 22 may result in the build up of charred biological matter on RF electrodes 22 (from contact with tissue and fluids e.g., blood) that impedes the flow of both thermal and electrical energy from RF electrodes 22 to adjacent tissue and causes an electrical impedance rise beyond a cutoff value set on RF energy source 24. A similar situation may result from the desiccation of tissue adjacent to RF electrodes 22. Cooling of RF electrodes 22 can be accomplished by the use of cooling media 35.

Additionally, electrodes 22 can be hollow and used to introduce electrolytic solutions into sphincter 16 and sphincter wall 17 through the use of ports 21''' disposed on electrodes 22 that are fluidically coupled to cooling media 35 and/or cooling media reservoir 35'. Suitable electrolytic solutions include saline; and solutions of calcium salts, potassium salts, and the like. Electrolytic solutions enhance the electrical conductivity of the targeted tissue at the treatment site 12. When a highly conductive fluid such as an electrolytic solution is infused into tissue the electrical resistance of the infused tissue is reduced, in turn, increasing the electrical conductivity of the infused tissue. As a result, there is little tendency for tissue surrounding RF electrode 22 to desiccate (a condition described herein that increases the electrical resistance of tissue) resulting in a large increase in the capacity of the tissue to carry RF energy.

One or more sensors 29 may be positioned adjacent to or on RF electrode 22 for sensing the temperature of sphincter tissue at treatment site 12. More specifically, sensors 29 permit accurate determination of the surface temperature and/or interior temperature of sphincter 16. This information can be used to regulate both the delivery of energy and cooling media 35 to sphincter 16. In various embodiments, sensors 29 can be positioned at any position on balloon 25, basket assembly 20 or at an RF electrode 22. Suitable sensors that may be used include but are not limited to, thermocouples, fiber optics, resistive wires, thermocouple IR detectors, and the like. Suitable thermocouples include T type with copper constantene, J type, E type and K types as are well known those skilled in the art.

Figure 5A:
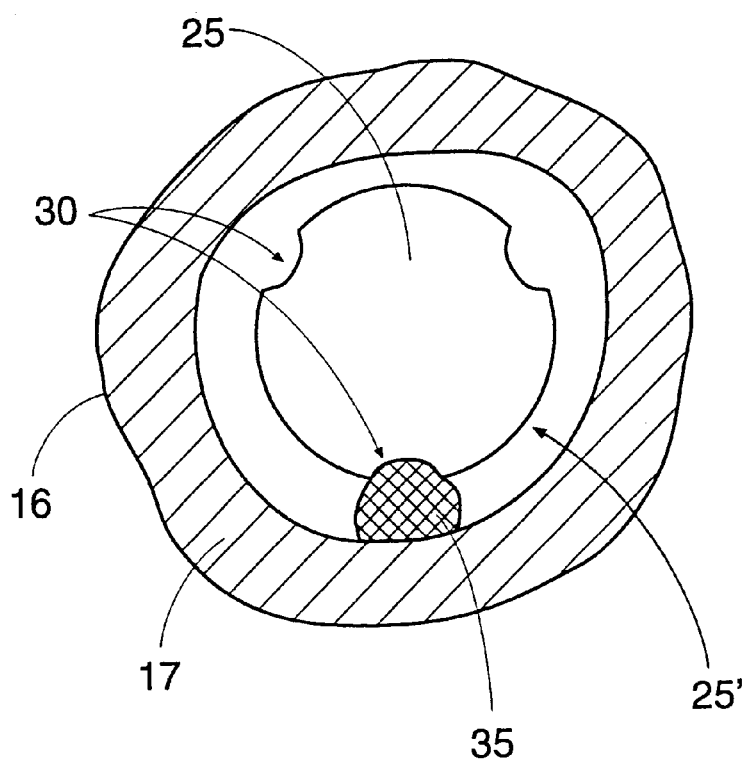
FIG. 5a is a cross-sectional view of an embodiment of the apparatus where the balloon has a deployed, non-circular, cross-sectional geometry that provides for the creation of axial flow channels adjacent to an exterior of the sphincter.
Figure 5B:
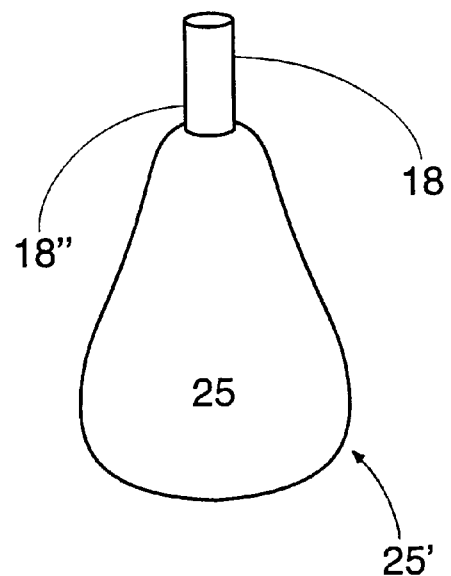
FIG. 5b is a cross-sectional view of an embodiment where the balloon has a pear shape.
Figure 5C:
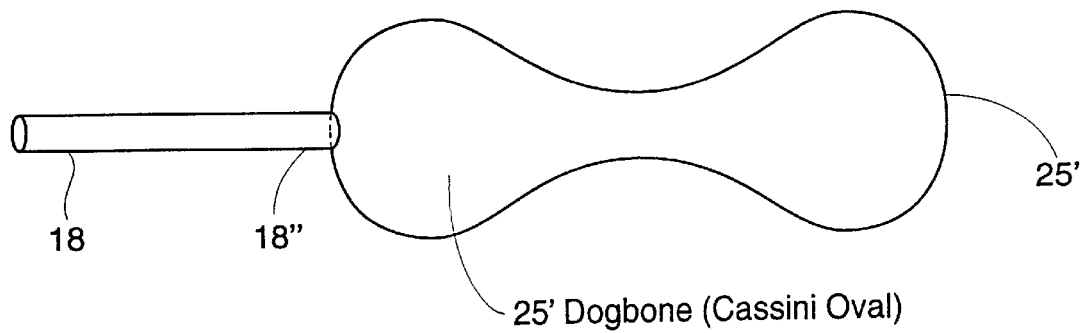
FIGS. 5c and 5d are cross-sectional views of embodiments of the invention where the balloon has a Cassini oval dogbone and oval shape.
Figure 5D:
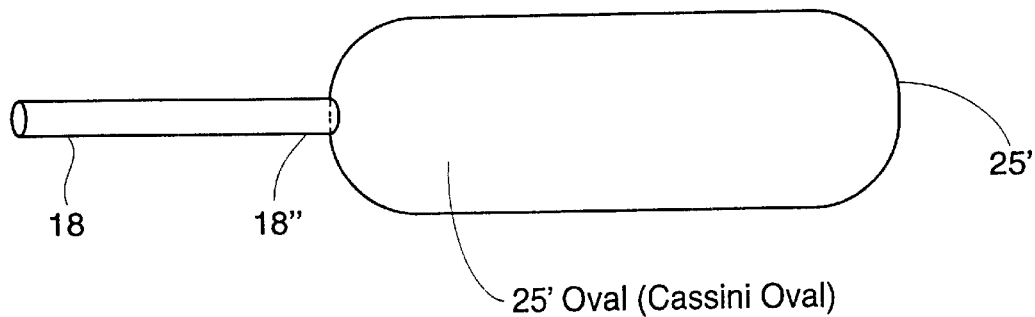

As illustrated in FIGS. 5a–5d, balloon 25 can have a variety of different deployed geometric configurations. Such configurations include, but are not limited to, spherical, football-shaped, cylindrical, channeled dog bone, oval and pear shapes. In the embodiment illustrated in FIG. 5a, balloon 25 has a non-circular cross-section which creates axial channels 30 between an exterior surface 25' of balloon 25 and sphincter 16. Axial channels 30 provide for the flow (in both proximal and distal directions) of any suitable fluid or media, such as a cooling media 35, at the interior surface of sphincter wall 17. In the embodiment illustrated in FIG. 5b, balloon 25 can be at least partially pear-shaped to approximately match the shape of the cardia of the stomach. In embodiments illustrated in FIGS. 5c and 5d, balloon 25 can have a Cassini oval shape, including embodiments where the Cassini oval has a dog bone (FIG. 5c) shape or oval shape (FIG. 5d). The dog bone shape facilitates maintaining the position of balloon 25 in a sphincter such as the LES or other stricture.

Figure 6:
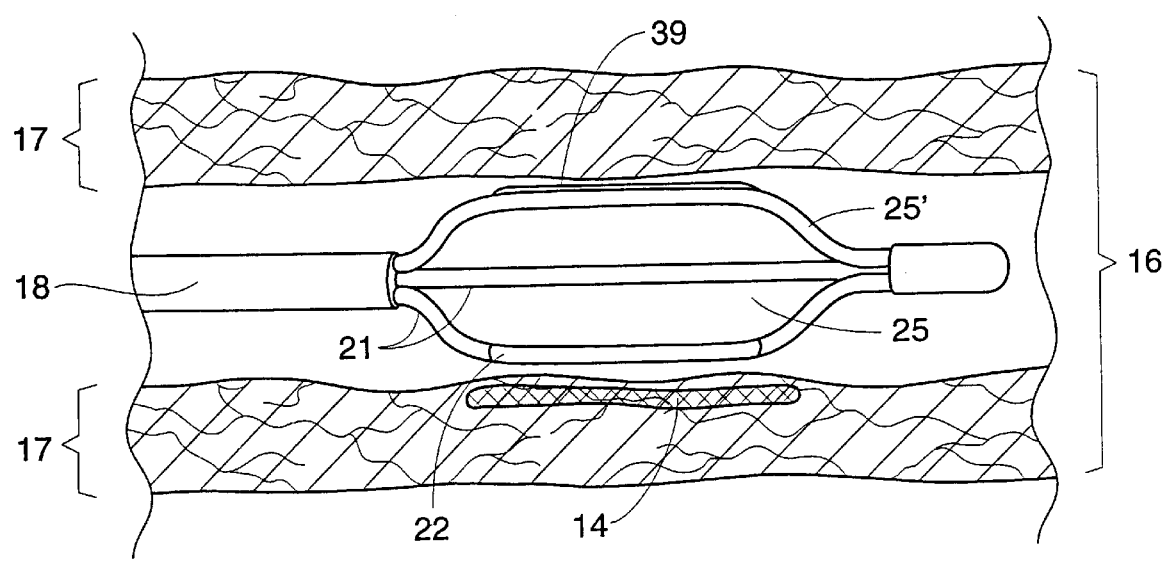
FIG. 6 is a cross-sectional view illustrates deployment of a balloon which has an elongated, substantially non-tapered geometry.

Another geometric configuration of balloon 25 is illustrated in FIG. 6. In this embodiment, balloon 25 has a substantially uniform interface surface 39 with sphincter wall 17. This uniformity provides substantially even contact between arms 21 and sphincter wall 17 in order to create uniform lesion 14 creation.

Figure 7:
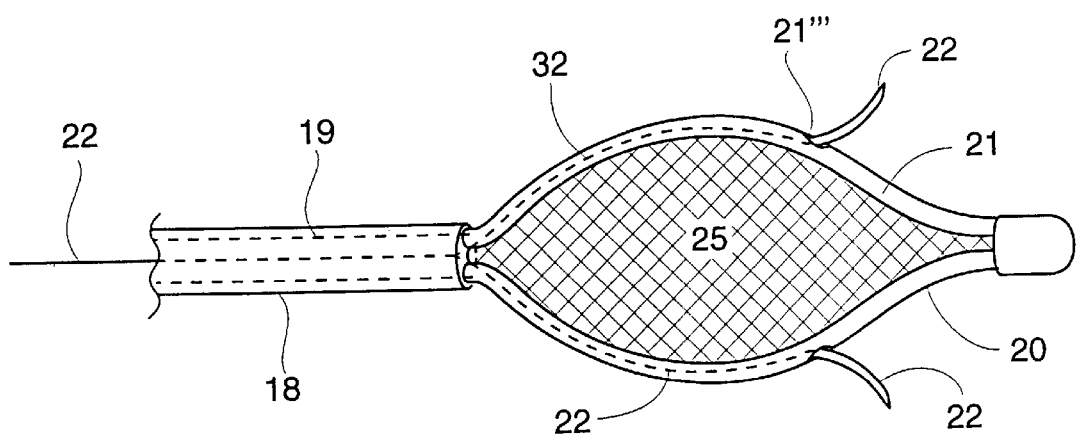
FIG. 7 is a cross-sectional view of the apparatus of FIG. 2A illustrating the coupling of an energy delivery device advancement and retraction member.

Referring now to FIG. 7, an electrode advancement and retraction member 32 (also called an electrode delivery member) is coupled to RF electrodes 22. In various embodiments electrode advancement and retraction member 32 can be an insulated wire, an insulated guide wire, a plastic-coated stainless steel hypotube with internal wiring or a plastic catheter with internal wiring, all of which are known to those skilled in the art. Retraction member 32 can also have a pre-shaped curve that can be directed by torquing member 32 or can be actively deflectable via the use of a pullwire or other mechanisms known in the art. Lumen 19 and retraction member 32 can be configured such that retraction member 32 is advanceable within lumen 19.

Figure 8:
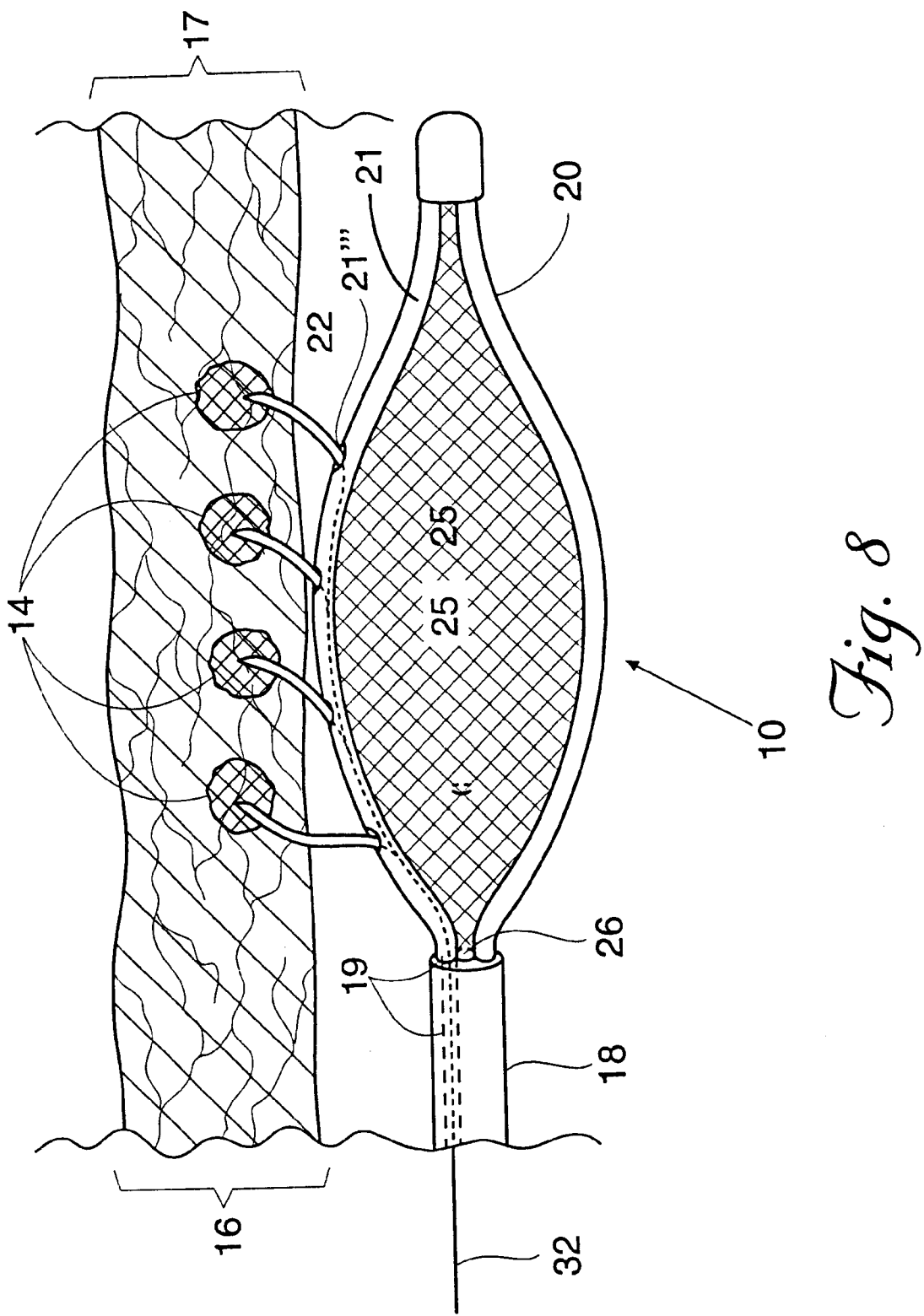
FIG. 8 is a cross-sectional view of an arm of the apparatus of FIG. 2A where all of the energy delivery devices positioned in the arm are advanced and retracted by a single advancement member.

In one embodiment, all RF electrodes 22 can be coupled to the same electrode advancement and retraction member 32. Alternatively, various numbers and groups of RF electrodes can be coupled to different electrode advancement and retraction members 32. In the embodiment illustrated in FIG. 8, all RF electrodes 22 in an arm 21 are coupled to the same electrode advancement and retraction member 32 and as such, can be advanced into sphincter 16 simultaneously. In this and related embodiments, retraction member 32 can be employed so as to produce multiple lesions 14 in the sphincter wall 17 while maintaining apparatus 10, in a substantially stationary position within sphincter 16. The configuration and use of retraction member 32 in this manner provides the advantage of reduced procedure time and a reduced likelihood of any trauma to the esophagus and surrounding tissue due to a reduced need to manipulate the apparatus within the esophagus.

Figure 9:
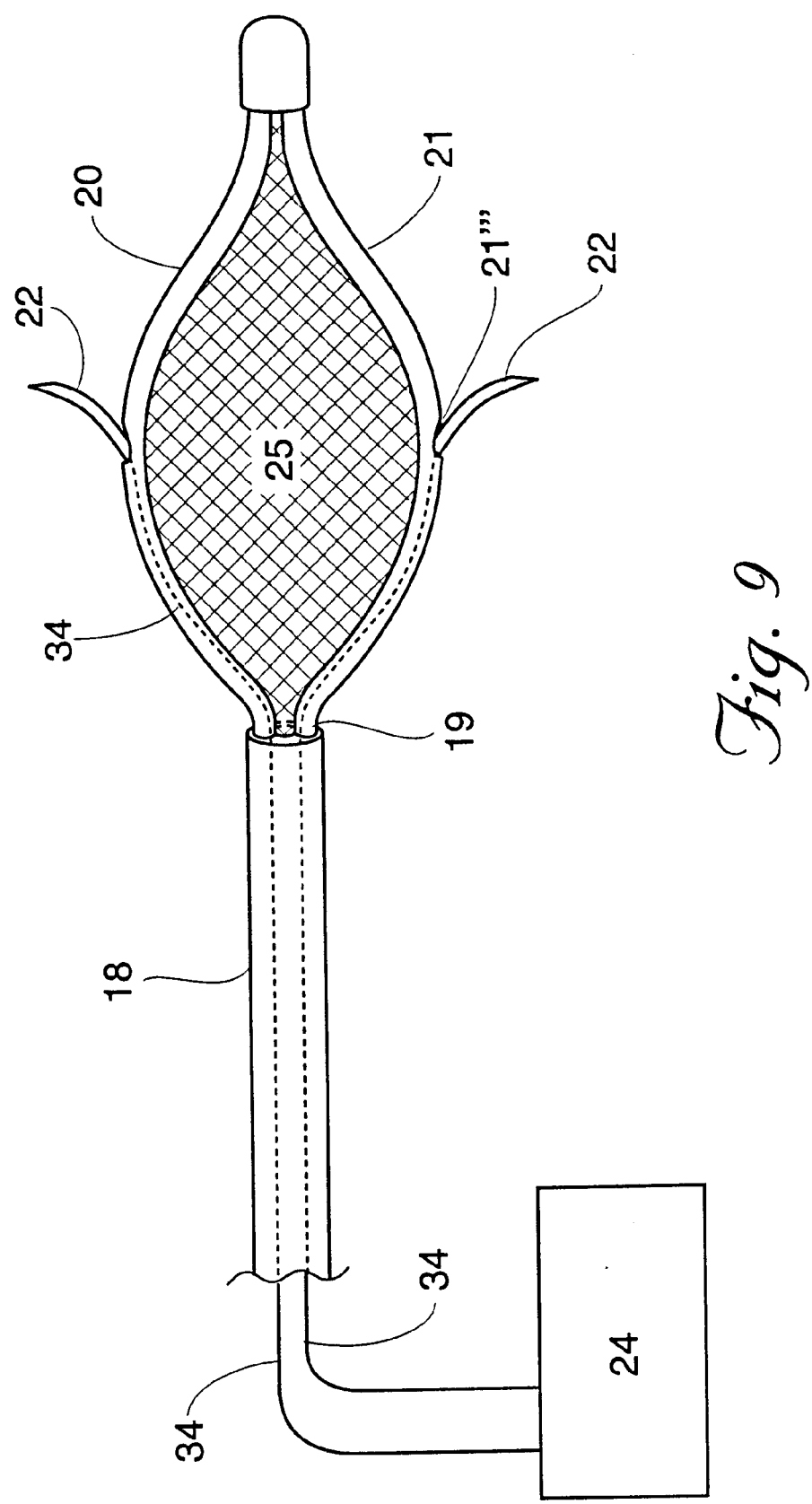
FIG. 9 is a cross-sectional view illustrating an embodiment of the invention having an insulated lumen that carries individual power wires that are coupled to separate energy delivery devices.

Referring now to FIG. 9, each RF electrode 22 can be coupled to a separate power wire 34 that is coupled to energy source 24. This permits RF electrodes to deliver energy non-simultaneously and offers the following advantages: i) individually tailored power delivery for each electrode, ii) individually temperature control for each electrode, iii) ability to compensate for differences in local tissue characteristics (e.g. electrical impedance, morphology, etc.) adjacent each electrode or variations in electrode penetration depth for the use of multiple electrodes, iv) more precise control of lesion location and size, v) generation of eccentric lesions or otherwise varying lesion locations and sizes, and vi) reduced procedure time. In alternative embodiments, energy delivery by multiple electrodes can be performed simultaneously through separate RF electrodes by utilizing a multichannel RF generator or by multiplexing the delivery of RF energy from a single RF energy source 24 to multiple RF electrodes 22 using multiplexing circuitry well known in the art. In still other embodiments, RF energy can be delivered sequentially to different electrode using a simple switch box known in the art.

Also when the energy source is RF, energy source 24, which will now be referred to as RF energy source 24, may have multiple channels, delivering separately modulated power to each RF electrode 22. This configuration reduces preferential heating that occurs when more energy is delivered to a zone of greater conductivity and less heating occurs around RF electrodes 22 which are placed into less conductive tissue. If the level of tissue hydration or the blood infusion rate in the tissue is uniform, a single channel RF energy source 24 may be used to provide power for generation of lesions 14 relatively uniform in size.

During introduction of apparatus 10, basket assembly 20 is in a contracted or non-deployed state. Once apparatus 10 is properly positioned at the treatment site 12, balloon 25 is inflated, basket assembly 20 is deployed (expanded) and RF electrodes 22 are then introduced into sphincter wall 17. The depth of needle penetration is selectable from a range of about 0.5 to 5 mms and can be accomplished by an indexed movable fitting coupled to shaft 18.

Referring now to FIGS. 10a and 10b, in another embodiment electrodes or needles 22 can be initially over-indexed to puncture through sphincter wall tissue to a first position and then retracted to a second or detent position where the needle tip is well within a desired penetration depth range in the esophageal wall tissue (e.g. 1–4 mms) for safe and effective tissue ablation of the desired treatment site 12. Such a configuration has the advantage of reducing or eliminating the occurrence of "tenting" of esophageal and/or sphincter tissue that may occur during electrode/needle penetration. In these and related embodiments, the advancement of electrode 22 can be controlled by the use of an electrode advancement mechanism 37 or fixture 37. As shown in FIGS. 10a and 10b, advancement mechanism 37 can include a ratchet mechanism or indexing mechanism, and the like. Alternatively as shown in FIG. 10c, mechanism 37 can include the use of a combination of mechanical stops and springs disposed in arm 21. In still other embodiments, mechanism 37 can include a combination one or more of the following: springs, stops, a ratchet mechanism or indexing mechanism. In various embodiments, advancement mechanism 37 can also be positioned at the proximal end 18' of the elongated shaft 18, on or within handpiece 31 or within arm 21.

RF energy flowing through sphincter or other tissue causes heating of the tissue due to absorption of the RF energy by the tissue and ohmic heating due to electrical resistance of the tissue. This heating can cause injury to the affected cells which can be substantial enough to cause cell death, a phenomenon also known as cell necrosis. For ease of discussion for the remainder of this application, cell injury will include all cellular effects resulting from the delivery of energy from RF electrode 22 up to, and including, cell necrosis. Cell injury can be accomplished as a relatively simple medical procedure with local anesthesia. In one embodiment, cell injury proceeds to a depth of approximately 1–4 mms from the surface of the mucosal layer 17' of sphincter 16 or that of an adjoining anatomical structure.

Figure 11:
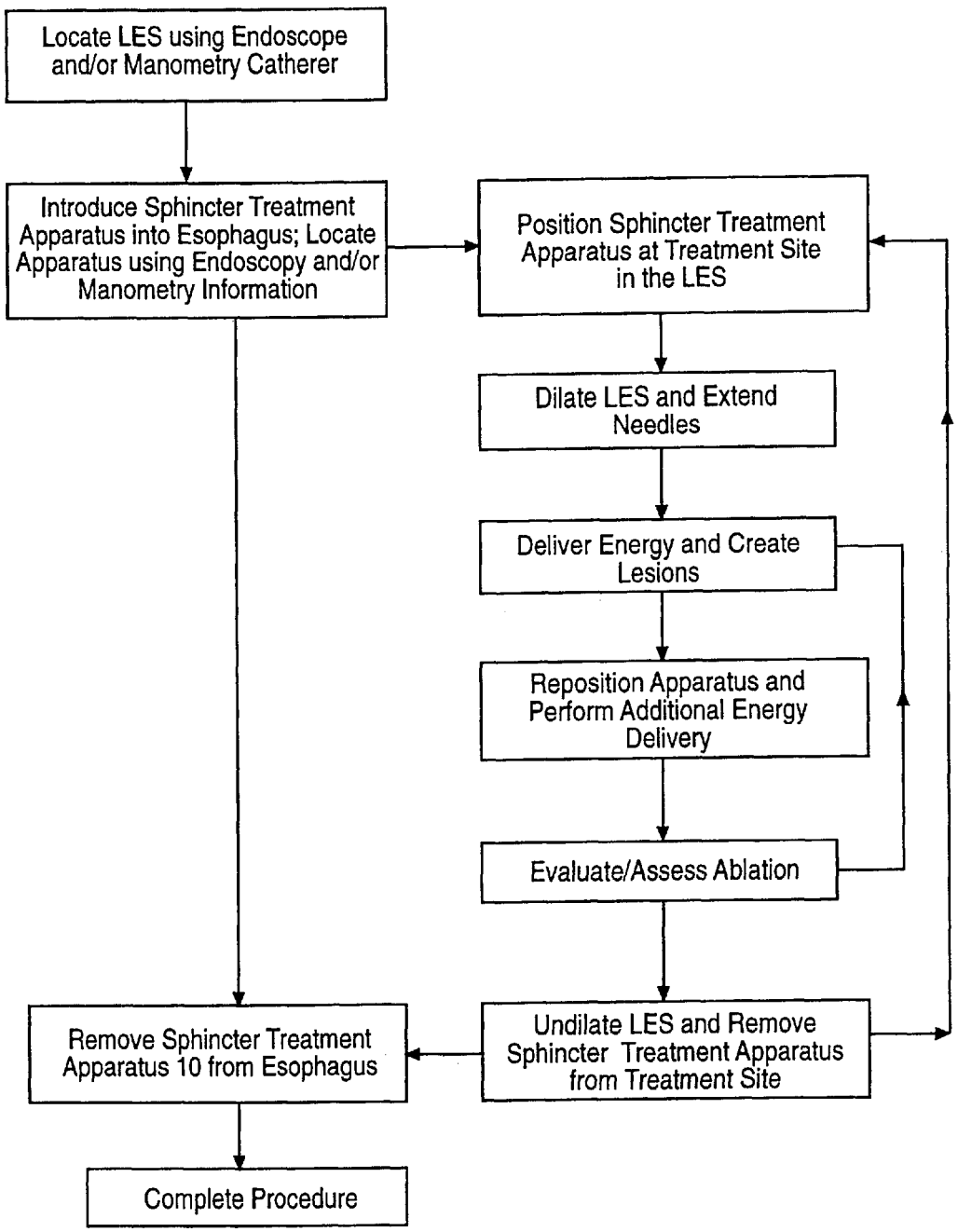
FIG. 11 is a flow chart illustrating a sphincter treatment method using the apparatus of the present invention.

FIG. 11 is a flow chart illustrating one embodiment of the procedure for using apparatus 10. In this embodiment, apparatus 10 is first introduced into the esophagus under local anesthesia. Apparatus 10 can be introduced into the esophagus by itself or through a lumen in an endoscope (not shown), such as disclosed in U.S. Pat. Nos. 5,448,990 and 5,275,608, both incorporated herein by reference, or similar esophageal access device known to those skilled in the art. Basket assembly 20 is expanded. Once introduced, basket assembly 20 is deployed by inflation of balloon 25 or other means. This serves to temporarily dilate the LES or sufficiently to efface a portion of or all of the folds of the LES. In an alternative embodiment, esophageal dilation and subsequent LES fold effacement can be accomplished by insufflation of the esophagus (a known technique) using gas introduced into the esophagus. Once treatment is completed, basket assembly 20 is returned to its predeployed or contracted state and apparatus 10 is withdrawn from the esophagus. This results in the LES returning to approximately its pretreatment state and diameter. It will be appreciated that the above procedure is applicable in whole or part to the treatment of other sphincters in the body.

The diagnostic phase of the procedure can be performed using a variety of diagnostic methods, including, but not limited to, the following: (i) visualization of the interior surface of the esophagus via an endoscope or other viewing apparatus inserted into the esophagus, (ii) visualization of the interior morphology of the esophageal wall using ultrasonography to establish a baseline morphology for the tissue to be treated, (iii) impedance measurement to determine the electrical conductivity between the esophageal mucosal layers 17' and apparatus 10, (iv) esophageal pressure measurement to determine location of the LES using esophageal manometry methods which may include the use of a manometry catheter and measurement system such as that sold by Medtronic Synectics (Stockholm, Sweden), (v) measurement and surface mapping of the electropotential of the LES during varying time periods which may include such physiological events as depolarization, contraction and repolarization of LES smooth muscle tissue. This latter technique is done to determine target treatment sites 12 in the LES or adjoining anatomical structures.

In the treatment phase of the procedure, the delivery of energy to treatment site 12 can be conducted under feedback control, manually or by a combination of both. Feedback control (described herein) enables apparatus 10 to be positioned and retained in the esophagus during treatment with minimal attention by the physician. RF electrodes 22 can be multiplexed in order to treat the entire targeted treatment site 12 or only a portion thereof. Feedback can be included and is achieved by the use of one or more of the following methods: (i) visualization, (ii) impedance measurement, (iii) ultrasonography, (iv) temperature measurement; and, (v) sphincter contractile force (e.g. pressure) measurement via manometry. The feedback mechanism permits the selected on-off switching of different RF electrodes 22 in a desired pattern, which can be sequential from one RF electrode 22 to an adjacent RF electrode 22, or can jump around between non-adjacent RF electrodes 22. Individual RF electrodes 22 can be multiplexed and volumetrically controlled by a controller.

The area and magnitude of cell injury in the LES or sphincter 16 can vary. However, it is desirable to deliver sufficient energy to the targeted treatment site 12 to be able to achieve tissue temperatures in the range of 55–95° C. and produce lesions 14 at depths ranging from 1–4 mms from the interior surface of the LES or sphincter wall 17. Typical energies delivered to the sphincter wall 17 include, but are not limited to, a range between 100 and 50,000 joules per RF electrode 22. It is also desirable to deliver sufficient energy such that the resulting lesions 14 have a sufficient magnitude and area of cell injury to cause an infiltration of lesion 14 by fibroblasts, myofibroblasts, macrophages and other cells involved in the tissue healing process. These cells cause a contraction of tissue around lesion 14, decreasing its volume and/or altering the biomechanical properties at lesion 14 so as to result in a tightening of LES or sphincter 16.

From a diagnostic standpoint, it is desirable to image the interior surface and wall 17 of the LES or other sphincter 16, including the size and position of created lesions 14. A map of these lesions 14 can inputted to a controller and used to direct the delivery of energy to the treatment site. This can be accomplished through the use of ultrasonography (a known procedure) which involves the use of an ultrasound energy source coupled to one or more ultrasound transducers that can be positioned on balloon 25 or basket assembly 20. An output is associated with the ultrasound energy source.

It is desirable that lesions 14 be predominantly located in the smooth muscle layer of selected sphincter 16 at the depths ranging from 1 to 4 mms from the interior surface of sphincter wall 17. However, lesions 14 can vary both in number and position within sphincter 16. It may be desirable to produce a pattern of multiple lesions 14 within the sphincter smooth muscle tissue in order to obtain a selected degree of tightening of the LES or other sphincter 16. Typical lesion patterns include, but are not limited to, (i) a concentric circle of lesions 14 formed at different levels in the smooth muscle layer evenly spaced along the radial axis of sphincter 16, (ii) a wavy or folded circle of lesions 14 at varying depths in the smooth muscle layer evenly spaced along the radial axis of sphincter 16, (iii) lesions 14 randomly distributed at varying depths in the smooth muscle, but evenly spaced in a radial direction; and, (iv) an eccentric pattern of lesions 14 in one or more radial locations in the smooth muscle wall. Accordingly, the depth of RF and thermal energy penetration sphincter 16 is controlled and selectable. The selective application of energy to sphincter 16 may be the even penetration of RF energy to the entire targeted treatment site 12, a portion of it, or applying different amounts of RF energy to different sites depending on the condition of sphincter 16. If desired, the area of cell injury can be substantially the same for every treatment event.

Figure 12:
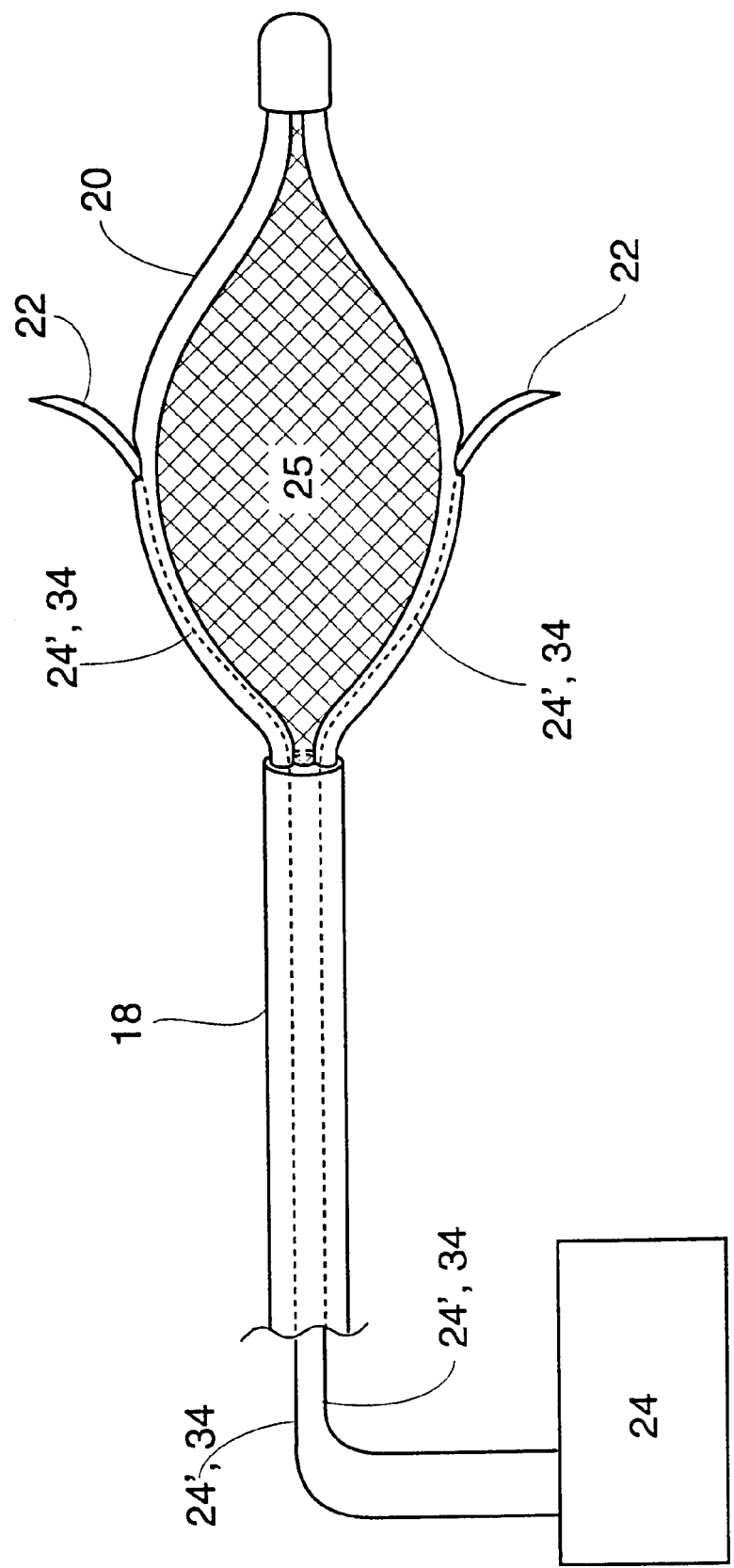
FIG. 12 is a cross-sectional view of a multi-channel RF generator useful with the apparatus of FIG. 2A.
Figure 13:
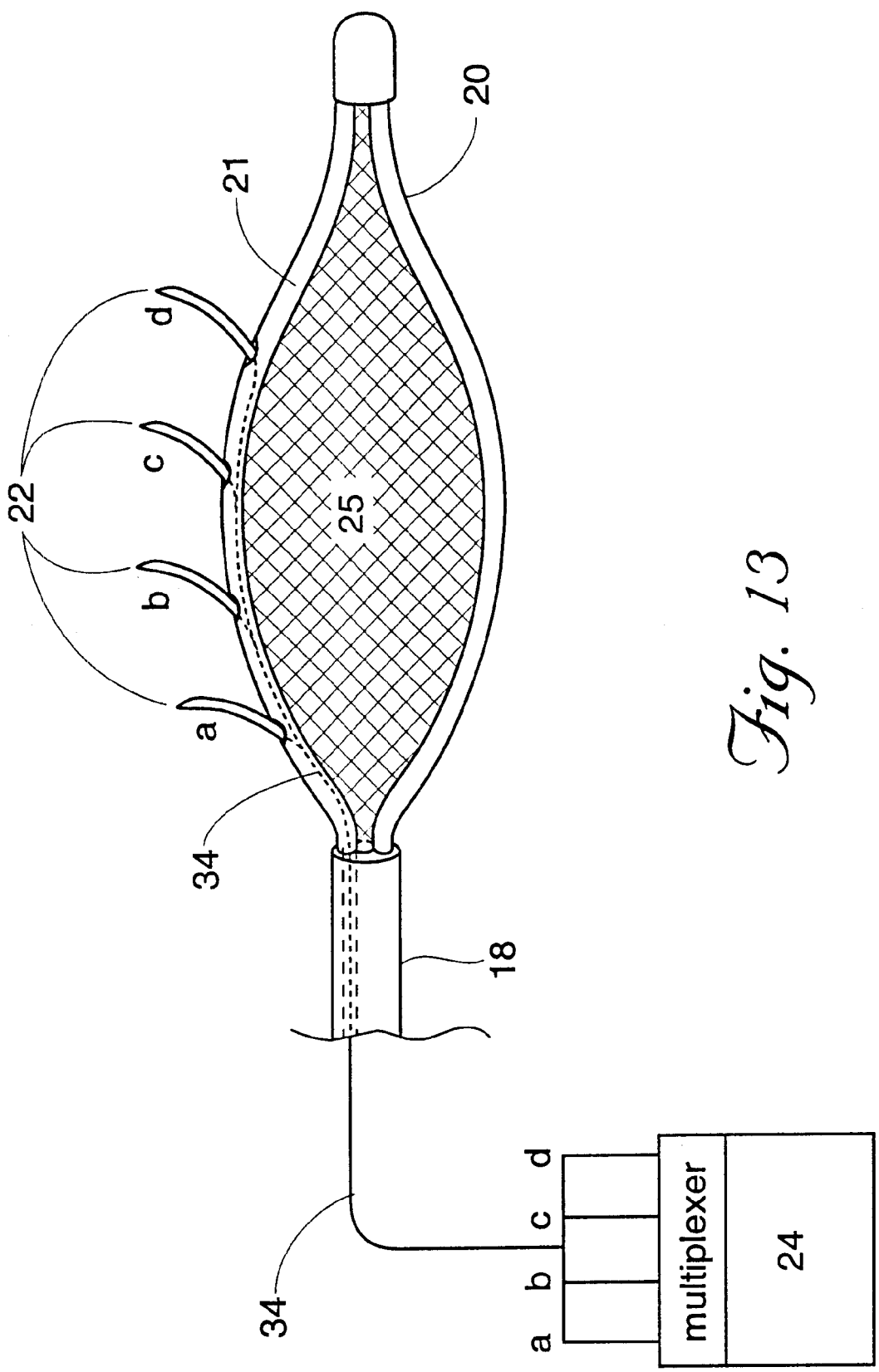
FIG. 13 is a cross-sectional view of an RF generator that sequentially delivers energy to distinct RF electrodes.

Referring now to FIG. 12, RF energy source 24 can include independent RF channels 24' that operate in parallel and are coupled to different RF electrodes 22. As illustrated in FIG. 13, RF energy source 24 can be configured (using circuitry known in the art such as a multiplexing circuit) to deliver energy to multiple RF electrodes 22 in a time-sharing fashion. This permits the delivery of RF energy to individual RF electrodes 22 for a selected period of time to each RF electrode 22 in a sequential manner.

Figure 14:
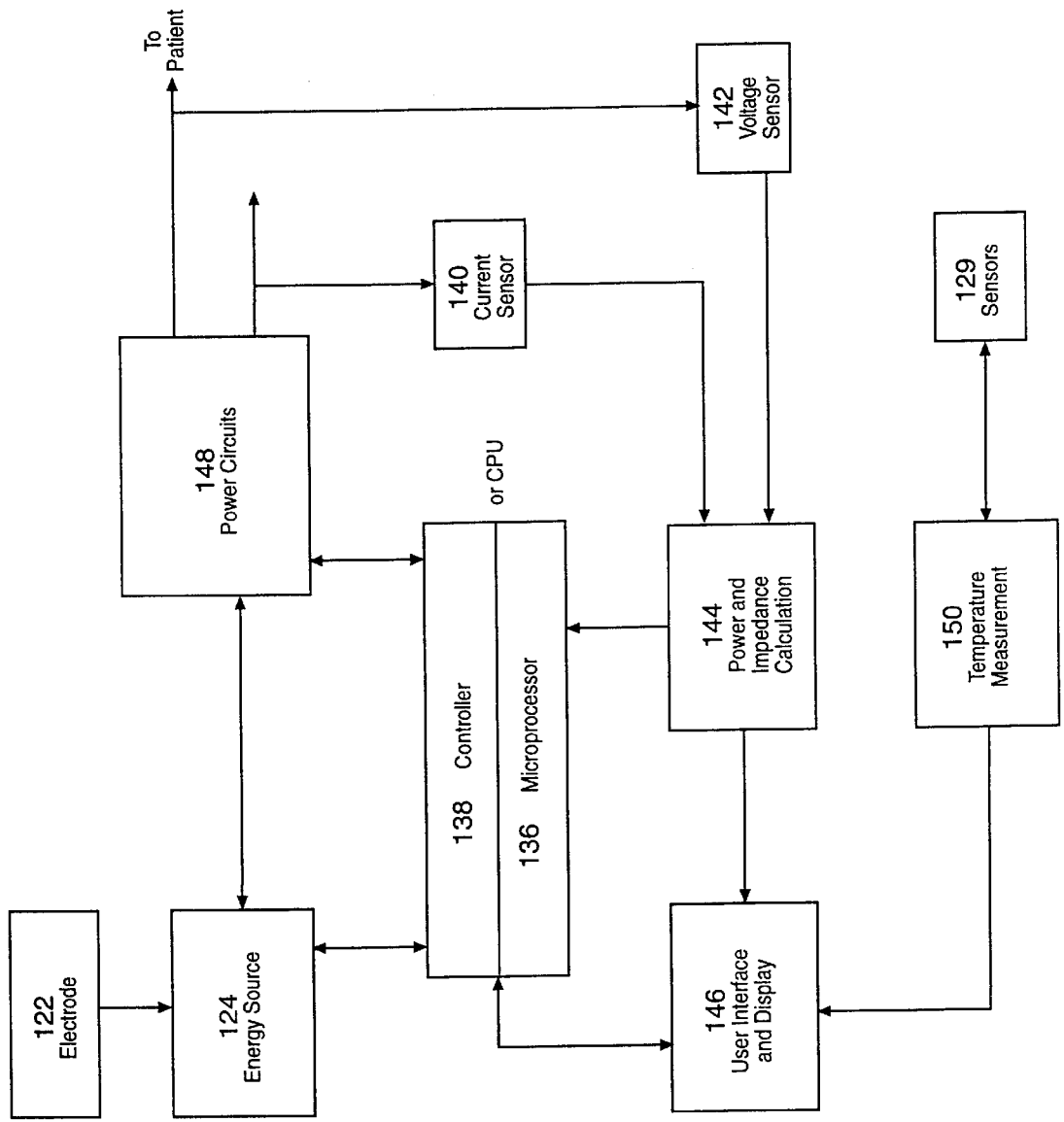
FIG. 14 depicts a block diagram of a feed back control system that can be used with the sphincter treatment apparatus of the present invention.

In one embodiment, apparatus 10 is coupled to an open or closed loop feedback system. Referring now to FIG. 14, an open or closed loop feedback system couples sensor 129 to energy source 124. In this embodiment, RF electrode 122 is one or more RF electrodes 122.

The temperature of the sphincter wall tissue, or of RF electrode 122 is monitored, and the output power of energy source 124 adjusted accordingly. The physician can, if desired, override the closed or open loop system. A microprocessor 136 can be included and incorporated in the closed or open loop system to switch power on and off, as well as modulate the power. The closed loop system utilizes microprocessor 136 to serve as a controller 138, monitor the temperature, adjust the RF power, analyze the result, refeed the result, and then modulate the power.

With the use of sensor 129 and the feedback control system a tissue adjacent to RF electrode 122 can be maintained at a desired temperature for a selected period of time without causing a shut down of the power circuit to RF electrode 122 due to the development of excessive electrical impedance at RF electrode 122 or adjacent tissue as is discussed herein. Each RF electrode 122 is connected to resources which generate an independent output. The output maintains a selected energy at RF electrode 122 for a selected length of time.

Current delivered through RF electrode 122 is measured by current sensor 140. Voltage is measured by voltage sensor 142. Impedance and power are then calculated at power and impedance calculation device 144. These values can then be displayed at user a interface and display 146. Signals representative of power and impedance values are received by controller 138.

A control signal is generated by controller 138 that is proportional to the difference between an actual measured value (e.g. an analog or digital signal indicative of temperature, power, etc.) and a desired value. The control signal is used by power circuits 148 to adjust the power output in an appropriate amount in order to maintain the desired power delivered at respective RF electrodes 122.

In a similar manner, temperatures detected at sensor 129 provide feedback for maintaining a selected power. The temperature at sensor 129 is used as a safety means to interrupt the delivery of energy when maximum pre-set temperatures are exceeded. The actual temperatures are measured at temperature measurement device 150, and the temperatures are displayed at user interface and display 146. A control signal is generated by controller 138 that is proportional to the difference between an actual measured temperature and a desired temperature. The control signal is used by power circuits 148 to adjust the power output in an appropriate amount in order to maintain the desired temperature delivered at the sensor 129. A multiplexer can be included to measure current, voltage and temperature, at the sensor 129, and energy can be delivered to RF electrode 122 in monopolar or bipolar fashion.

Controller 138 can be a digital or analog controller, or a computer with software. When controller 138 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 146 includes operator controls and a display. Controller 138 can be coupled to imaging systems including, but not limited to, ultrasound, CT scanners, X-ray, MRI, mammographic X-ray and the like. Further, direct visualization and tactile imaging can also be utilized.

The output of current sensor 140 and voltage sensor 142 are used by controller 138 to maintain a selected power level at RF electrode 122. The amount of RF energy delivered controls the amount of power. A profile of the power delivered to electrode 122 can be incorporated in controller 138 and a preset amount of energy to be delivered may also be profiled.

Circuitry, software and feedback to controller 138 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 129.

Figure 15:
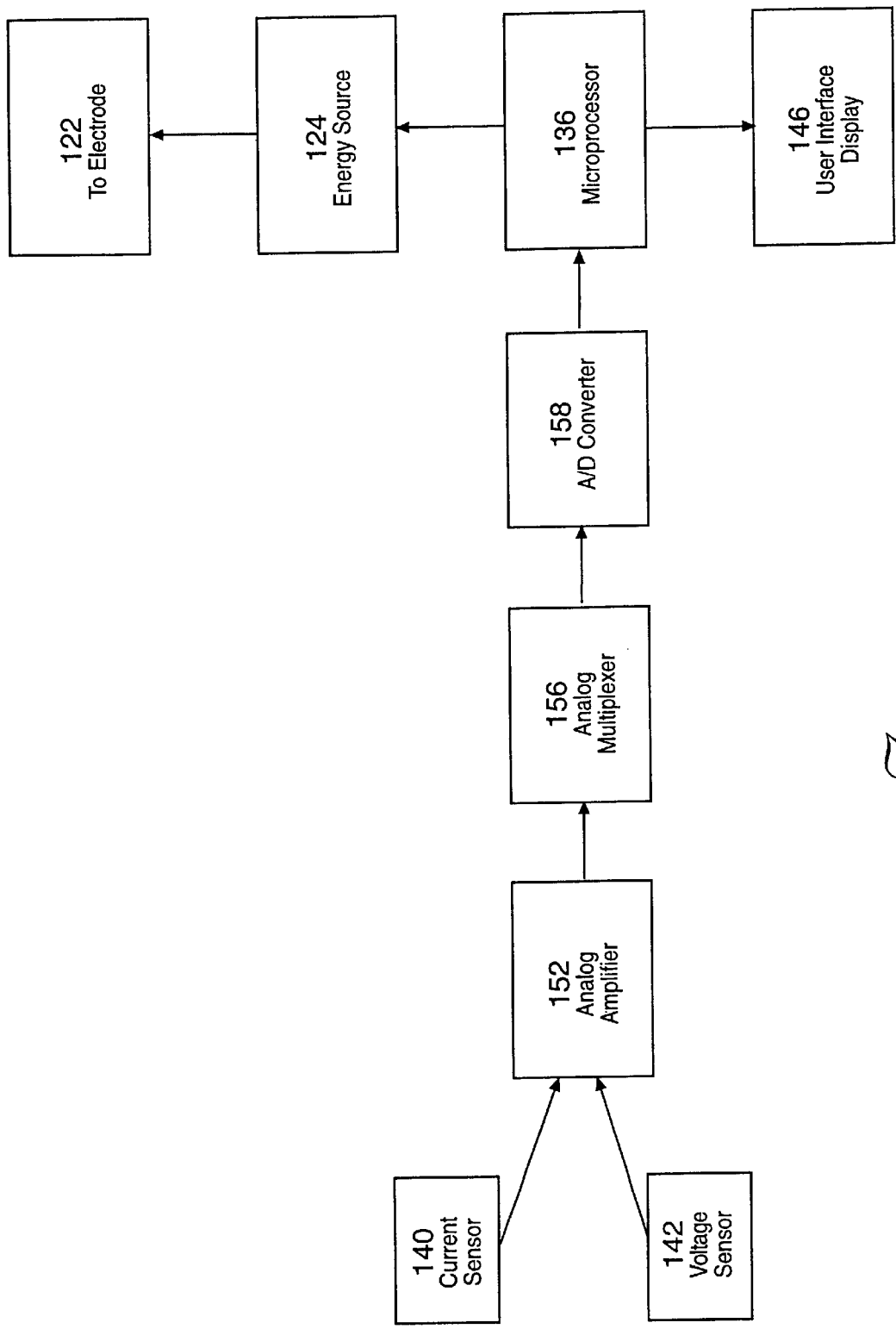
FIG. 15 depicts a block diagram of an analog amplifier, analog multiplexer and microprocessor used with the feedback control system of FIG. 14.

Referring now to FIG. 15, current sensor 140 and voltage sensor 142 are connected to the input of an analog amplifier 152. Analog amplifier 152 can be a conventional differential amplifier circuit for use with sensor 129. The output of analog amplifier 152 is sequentially connected by an analog multiplexer 156 to the input of A/D converter 158. The output of analog amplifier 152 is a voltage which represents the respective sensed temperatures. Digitized amplifier output voltages are supplied by A/D converter 158 to microprocessor 136. Microprocessor 136 may be a type 68HCII available from Motorola or a Pentium® type available from the Intel® Corporation. However, it will be appreciated that any suitable microprocessor or general purpose digital or analog computer can be used to calculate impedance or temperature.

Microprocessor 136 sequentially receives and stores digital representations of impedance and temperature. Each digital value received by microprocessor 136 corresponds to different temperatures and impedances.

Calculated power and impedance values can be indicated on user interface and display 146. Alternatively, or in addition to the numerical indication of power or impedance, calculated impedance and power values can be compared by microprocessor 136 to power and impedance limits. When the values exceed predetermined power or impedance values, a warning can be given on user interface and display 146, and additionally, the delivery of RF energy can be reduced, modified or interrupted. A control signal from microprocessor 136 can modify the power level supplied by energy source 124.

Figure 16:
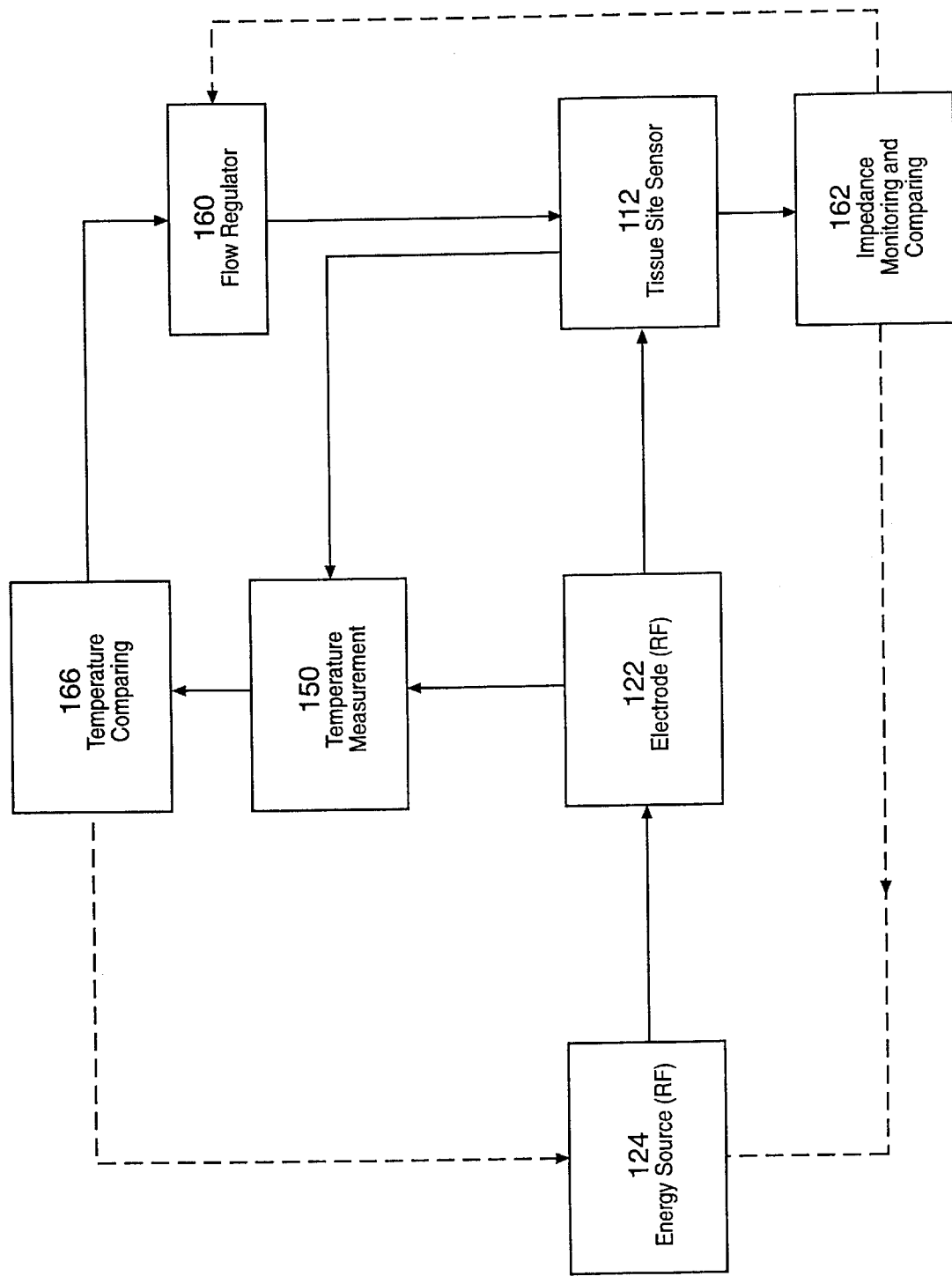
FIG. 16 depicts a block diagram of the operations performed in the feedback control system of FIG. 14.

FIG. 16 illustrates a block diagram of a temperature and impedance feedback system that can be used to control the delivery of energy to tissue site 112 by energy source 124 and the delivery of cooling solution to RF electrode 122 and/or tissue site 112 by flow regulator 160. Energy is delivered to RF electrode 122 by energy source 124, and applied to tissue site 112. A monitor 162 ascertains tissue impedance, based on the energy delivered to tissue, and compares the measured impedance value to a set value. If the measured impedance exceeds the set value, a disabling signal 164 is transmitted to energy source 124, ceasing further delivery of energy to RF electrode 122. If measured impedance is within acceptable limits, energy continues to be applied to the tissue.

The control of the delivery of a cooling solution to RF electrode 122 and/or tissue site 112 is done in the following manner. During the application of energy, temperature measurement device 150 measures the temperature of tissue site 112 and/or RF electrode 122. A comparator 166 receives a signal representative of the measured temperature and compares this value to a pre-set signal representative of the desired temperature. If the tissue temperature is too high, comparator 166 sends a signal to a flow regulator 160 (connected to an electronically controlled micropump, not shown) representing a need for an increased cooling solution flow rate. If the measured temperature has not exceeded the desired temperature, comparator 166 sends a signal to flow regulator 160 to maintain the cooling solution flow rate at its existing level.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A sphincter treatment apparatus comprising:
    an elongated member having at least one lumen including an inflation lumen,
    a basket assembly including a first and a second arm, the basket assembly being coupled to the elongated member and having a deployed and a non-deployed configuration,
    an inflatable member coupled to the elongated member and positioned in an interior of the basket assembly, the inflatable member being coupled to the inflation lumen, the inflatable member having a deployed and a non-deployed state, wherein in the deployed state the inflatable member expands the basket assembly to the basket assembly deployed configuration, and
    an energy delivery device coupled to the basket assembly and configured to be advanceable into tissue to deliver energy to a selected treatment site.

2. The apparatus of claim 1 wherein the energy delivery device is positioned on an exterior surface of the basket assembly.

3. The apparatus of claim 1 wherein the energy delivery device is integral to the basket assembly.

4. The apparatus of claim 1 wherein the energy delivery device is disposed in the basket assembly.

5. The apparatus of claim 4 wherein the energy delivery device is disposed on an interior surface of the basket assembly.

6. The apparatus of claim 1 wherein the energy delivery device includes a tissue-piercing distal end.

7. The apparatus of claim 6 wherein the energy delivery device is a radiofrequency electrode.

8. The apparatus of claim 7 wherein the radiofrequency electrode is a needle electrode.

9. The apparatus of claim 7 wherein the energy delivery device includes a plurality of radiofrequency electrodes.

* * * * *